US010028823B2

(12) United States Patent
Akura

(10) Patent No.: US 10,028,823 B2
(45) Date of Patent: Jul. 24, 2018

(54) ACCOMMODATING INTRAOCULAR LENS

(71) Applicants: Frontier Vision Co., Ltd., Hyogo (JP); Junsuke Akura, Wakayama (JP)

(72) Inventor: Junsuke Akura, Wakayama (JP)

(73) Assignee: MIRAI EYE INC., Hyogo (JP)

( * ) Notice: Subject to any disclaimer, the term of this patent is extended or adjusted under 35 U.S.C. 154(b) by 123 days.

(21) Appl. No.: 15/103,610

(22) PCT Filed: Dec. 10, 2014

(86) PCT No.: PCT/JP2014/082735
§ 371 (c)(1),
(2) Date: Jun. 10, 2016

(87) PCT Pub. No.: WO2015/087930
PCT Pub. Date: Jun. 18, 2015

(65) Prior Publication Data
US 2016/0310264 A1    Oct. 27, 2016

(30) Foreign Application Priority Data
Dec. 13, 2013    (JP) .................................. 2013-257870

(51) Int. Cl.
*A61F 2/16*    (2006.01)
(52) U.S. Cl.
CPC ........ *A61F 2/1635* (2013.01); *A61F 2/16015* (2015.04); *A61F 2/1648* (2013.01);
(Continued)
(58) Field of Classification Search
CPC .. A61F 2/1694; A61F 2/1635; A61F 2/16015; A61F 2/1627; A61F 2002/1682;
(Continued)

(56) References Cited

U.S. PATENT DOCUMENTS 7,871,437 B2 *   1/2011  Hermans ............... A61F 2/1613
                                                        623/6.38
8,048,155 B2 *  11/2011  Shadduck ............. A61F 2/1648
                                                        623/6.13
(Continued)

FOREIGN PATENT DOCUMENTS

JP        2006-516002 A      6/2006
JP         2007-89810 A      4/2007
(Continued)

OTHER PUBLICATIONS

International Search Report dated Mar. 10 2015, issued in corresponding PCT/JP2014/082735, 2 pages.
(Continued)

*Primary Examiner* — David H Willse
*Assistant Examiner* — Javier Blanco
(74) *Attorney, Agent, or Firm* — Millen, White, Zelano & Branigan, P.C.; William Nixon

(57) ABSTRACT

An intraocular lens includes a lens capsule expanding device and an optical portion. The lens capsule expanding device includes a front supporting portion to make contact with an inner surface of an anterior capsule. A rear supporting portion provided on a rear side of the front supporting portion makes contact with an inner surface of a posterior capsule while facing the front supporting portion. A connecting portion connects the front supporting portion and the rear supporting portion so as to have biasing force in a direction of separating the front supporting portion and the rear supporting portion from each other. Due to the biasing force, the front supporting portion presses the inner surface of the anterior capsule and the rear supporting portion presses the inner surface of the posterior capsule. The optical portion changes the curvature of a central portion according to movement of the connecting portion.

3 Claims, 13 Drawing Sheets

(52) U.S. Cl.
CPC .......... *A61F 2/1694* (2013.01); *A61F 2/1627* (2013.01); *A61F 2002/1682* (2015.04); *A61F 2250/0003* (2013.01)

(58) Field of Classification Search
CPC ............ A61F 2/1648; A61F 2250/0003; A61F 2/1624; A61F 2002/16901
See application file for complete search history.

(56) References Cited

U.S. PATENT DOCUMENTS

| | | |
|---|---|---|
| 2004/0082993 A1 | 4/2004 | Woods |
| 2007/0156236 A1* | 7/2007 | Stenger ................ A61F 2/1635 623/6.13 |
| 2009/0012609 A1 | 1/2009 | Geraghty et al. |
| 2009/0043384 A1 | 2/2009 | Niwa et al. |
| 2009/0306774 A1 | 12/2009 | Park |
| 2010/0016963 A1 | 1/2010 | Park |
| 2011/0071628 A1* | 3/2011 | Gross ................... A61F 2/1629 623/6.51 |
| 2011/0313522 A1* | 12/2011 | Hayes ................... A61F 2/1602 623/6.43 |
| 2012/0296424 A1* | 11/2012 | Betser ................... A61F 2/1613 623/6.13 |
| 2012/0310345 A1* | 12/2012 | Olcina Portilla ..... A61F 2/1613 623/6.46 |
| 2013/0317607 A1 | 11/2013 | Deboer et al. |

FOREIGN PATENT DOCUMENTS

| | | |
|---|---|---|
| JP | 2010-502358 A | 1/2010 |
| JP | 2010-520011 A | 6/2010 |

OTHER PUBLICATIONS

English translation Abstract of JP2010-520011A published Jun. 10, 2010 (1 page).
English translation Abstract of JP2007-89810A published Apr. 12, 2007 (1 page).
English translation Abstract of JP2010-502358A published Jan. 28, 2010 (1 page).

* cited by examiner

ACCOMMODATING INTRAOCULAR LENS

TECHNICAL FIELD

The present invention relates to an accommodating intraocular lens which is inserted into a lens capsule of which the anterior capsule is incised during ophthalmic surgeries such as an extracapsular extraction surgery performed as a part of a cataract surgery, a refractive correction surgery, or a presbyopia correction surgery.

BACKGROUND ART

Generally, the focus accommodation of the human eyes (hereinafter simply referred to as "accommodation") is realized by changing the thickness of the lens. As illustrated in FIG. 18, a lens L is a convex transparent member having a diameter of approximately 9 to 10 mm and a thickness of approximately 4 to 5 mm and exerting a lens function, and is fixed to a ciliary body C by Zinn's zonules Z in such a manner as to be arranged on the rear side of the iris I in a state of being encapsulated by a lens capsule S.

A detailed accommodation mechanism will be described. For example, when a person looks at a distant object, as illustrated in FIG. 18(a), the ciliary muscles Cm of the ciliary bodies C are relaxed and the ciliary bodies C are at positions retracted in a direction away from the lens capsule S. In this state, relatively strong tension is generated in the Zinn's zonules Z positioned between the ciliary bodies C and the lens equators Se. As a result, the lens equators Se are pulled in a radially outward direction to deform the lens L in such away as to decrease the thickness thereof. Accordingly, the thickness of the lens L in the lens capsule S decreases, whereby the focus accommodation during distance vision is realized.

On the other hand, when accommodation is realized to view a near object, as illustrated in FIG. 18(b), the ciliary muscles Cm of the ciliary bodies C are contracted so that the ciliary bodies C protrude centripetally (toward the lens equators Se) and the ciliary bodies C are positioned in a direction closer to the lens capsule S. As a result, since the tension of the Zinn's zonules Z decreases, the thickness of the lens L increases due to the elasticity inherent to the lens, whereby the focus accommodation during near vision is realized. During this focus accommodation, it is known that the closer a portion is located in relation to the center of the anterior capsule Sf, the more the portion is likely to be movable, whereas the posterior capsule Sb is rarely movable.

As described above, the thickness of the lens is changed according to contraction and relaxation of the ciliary muscles of the ciliary bodies to refract light entering the eyes, whereby the focus accommodation is realized. In this accommodation mechanism, it is known that the contraction and relaxation functions of the ciliary muscles of the ciliary bodies are maintained satisfactorily in old ages in the same manner as in young ages. On the other hand, it is also known that, since the contents of the lens and the lens capsule become hardened in old ages and lose flexibility, thus making the thickness of the lens rarely change, the ability (hereinafter referred to as accommodation power) to accommodate the focus range freely from distance vision to near vision is lost (this is referred to as presbyopia).

By the way, a disease called a cataract which is a clouding of the lens mainly resulting from aging is one of the diseases occurring in the lens, and many patients have cataract surgery to treat their cataracts. This surgery generally uses a method in which the anterior capsule is incised in a circular form to create a circular hole, the contents of the cloudy lens are extracted from the hole according to phacoemulsification, and an intraocular lens is inserted into a transparent lens capsule while leaving only the lens capsule with the circular hole formed therein. The cataract surgery based on this method has been currently applied to more than one million patients in Japan every year and more than 3 million patients in the United States of America every year, and the intraocular lenses used for this surgery are generally monofocal lenses.

However, since the monofocal lenses are generally formed of a material such as polymethylmethacrylate (PMMA), silicon, or acryl, and it is not possible to change the thickness of the monofocal lens itself, the loss of the accommodation power after the surgery is unavoidable. In contrast, multifocal lenses which are arranged in a refractive multifocal lens having portions having different refractive powers formed concentrically in an optical portion and a diffractive multifocal lens having a structure causing an optical diffraction phenomenon formed in an optical portion so as to disperse and capture light entering into the eyes are arranged as multifocal lenses for distance vision and near vision (in some cases, for intermediate vision). However, these multifocal intraocular lenses have not reached a sufficient point of satisfaction to meet the demands of patients because there are reports that some patients experience halos where a ring of light appears around an object, trouble such as glare with bright light, a decrease in vision, and insufficient contrast sensitivity.

Moreover, in recent years, as an intraocular lens capable of exerting an accommodation function by a method different from the above-mentioned method, an accommodating intraocular lens including an optical portion formed of a convex lens and two joint-type connection arms arranged in such a manner as to come into contact with the inner side of a lens equator so that accommodation is realized by the optical portion moving back and forth is known (see Patent Document 1 below). In this accommodating intraocular lens, the connection arm is attached to the optical portion at a first position on the connection arm and works harmoniously with the movement of the equator of the lens capsule to which the contraction and relaxation of the ciliary muscles of the ciliary bodies are transmitted via the Zinn's zonules at a second position on the connection arm.

On the other hand, a number of ring-shaped lens capsule expanding devices which are used for expanding the lens capsule before inserting an intraocular lens during cataract surgery have been proposed. These ring-shaped lens capsule expanding devices come in two types depending on the purpose.

One example is called a capsular tension ring (a lens capsule expansion ring) which is an open ring formed in a C-shape. This ring is inserted from the inner side into the lens equators in which the Zinn's zonules are weak and ruptured to expand the lens equators outward to create a round shape.

The other example is called an equator ring which is formed in an O-shape. This ring is a relatively thick closed ring (continuous ring) of which the cross-section has sharp edges such as a square. This ring is arranged on an inner side of the lens equators to form a strong bent portion in the lens capsule to prevent the growth and entrance of lens epithelial cells.

CITATION LIST

Patent Document

Patent Document 1: Japanese Unexamined Patent Application Publication No. 11-47168

SUMMARY OF THE INVENTION

Problem to be Solved by the Invention

However, the focus accommodation function of the human eyes is exerted based on the contraction and relaxation of the ciliary muscles of the ciliary bodies. Therefore, in order to move the optical portion of an intraocular lens in a front-back direction, it is necessary to deform the lens capsule by accurately transmitting slight contraction and relaxation of the ciliary muscles of the ciliary bodies. To realize this, it is important that the Zinn's zonules that transmit the contraction and relaxation of the ciliary muscles of the ciliary bodies to the lens capsule continuously have tension of moderate strength, and as a result, the lens capsule has moderate strength.

In this regard, a conventional accommodating intraocular lens does not act such that the Zinn's zonules continuously have tension of moderate strength. Therefore, the slight contraction and relaxation of the ciliary muscles of the ciliary bodies are not accurately transmitted to the lens capsule and are not accurately converted to the movement of the optical portion in the front-back direction. Moreover, it is difficult to accurately exert the accommodation function of the intraocular lens arranged therein.

Similarly, the ring-shaped lens capsule expanding device can adjust the position of the lens equator and create a strong bent portion in the lens capsule. However, it is difficult to continuously maintain tension of moderate strength in the Zinn's zonules. Moreover, the ring-shaped lens capsule expanding device expands the lens equator outward to weaken the tension of the Zinn's zonules. For this reason, the slight contraction and relaxation of the ciliary muscles of the ciliary bodies are not accurately transmitted to the lens capsule, and it is difficult to exert the accommodation function of the accommodating intraocular lens.

Further, in a large number of conventional ring-shaped lens capsule expanding devices, the connection arm and the ring-shaped lens capsule expanding device itself are fixed in such a manner to be in contact with the inner side of the lens equator. Thus, the anterior capsule and the posterior capsule adhere to each other to block the lens equator with time. In recent years, it has been found that, since a secondary cataract rarely occurs when hydatoid always flows into the lens equator, the hydatoid has an effect of suppressing the growth of lens epidermal cells. However, in these conventional intraocular lenses, since the lens equator is not exposed to hydatoid, lens epidermal cells grow in the lens equator to cause fibroplasia, thus creating a state in which a secondary cataract occurs easily.

When a secondary cataract occurs, since the central portion of the lens capsule becomes cloudy and light can rarely pass through the lens capsule, the visual power decreases and the lens equator adheres in the front-back direction to cause fibroplasia, which results in hardening of the equator. Moreover, the joint-type connection arm of the accommodating intraocular lens is fixed by fibers and becomes immovable, which prevents exertion of the accommodation function of the accommodating intraocular lens.

The present invention was made in view of the aforementioned problems and aims to provide an accommodating intraocular lens capable of exerting the focus accommodation power accurately and sufficiently and preventing the occurrence of a secondary cataract.

Solution to Problems

In order to attain the object, an accommodating intraocular lens according to the present invention is an accommodating intraocular lens inserted into a lens capsule from which contents are removed during an ophthalmic surgery, including: a lens capsule expanding device; and an optical portion which is elastically deformable, the lens capsule expanding device including: a front supporting portion provided in such a manner as to make contact with an inner surface of an anterior capsule so as to pass light toward a rear side; a rear supporting portion provided on a rear side of the front supporting portion in such a manner as to make contact with an inner surface of a posterior capsule while facing the front supporting portion so as to pass light from the front side toward a rear side; and a connecting portion connecting the front supporting portion and the rear supporting portion in such a manner as to have biasing force in a direction of separating the front supporting portion and the rear supporting portion from each other, wherein due to the biasing force of the connecting portion, the front supporting portion presses the inner surface of the anterior capsule and the rear supporting portion presses the inner surface of the posterior capsule, and the optical portion is locked directly or indirectly to the connecting portion in such a manner that the optical portion is surrounded by the connecting portion of the lens capsule expanding device, and force is applied directly or indirectly from the connecting portion according to movement of the connecting portion when the front supporting portion and the rear supporting portion move in a direction closer to or away from each other with movement of the lens capsule whereby a curvature of the optical portion is changed.

According to this configuration, due to the biasing force of the connecting portion, the front supporting portion presses the inner surface of the anterior capsule and the rear supporting portion presses the inner surface of the posterior capsule. As a result, the peripheral portion of the lens equator tries to extend and expand in the front-back direction and the lens equator expands. At the same time, the lens equator moves centripetally and the diameter of the lens equator decreases. Due to this, the Zinn's zonules are pulled in both directions toward the lens capsule and the ciliary bodies and tension of moderate strength is continuously applied to the Zinn's zonules. As a result, moderate tension is applied to the lens capsule. Thus, the Zinn's zonules can transmit the slight contraction and relaxation of the ciliary muscles of the ciliary bodies to the lens capsule with high accuracy, and accordingly, the accommodation function of the optical portion disposed therein can be exerted with high accuracy.

Moreover, when the front supporting portion is formed in an open state like a ring form, hydatoid flows from an anterior capsule incision portion to the space between the front supporting portion and the connecting portion and flows into the lens capsule, and the lens equator is exposed to the hydatoid. Thus, the growth or fibroplasia of the lens epithelial cells in the lens equator is suppressed and the occurrence of the secondary cataract can be prevented.

Further, when the front supporting portion and the rear supporting portion move in the direction closer to or away from each other according to the movement of the lens capsule, force is applied directly or indirectly from the connecting portion according to the movement of the connecting portion and the curvature of the optical portion changes. Thus, it is possible to exert the focus accommodation power with high accuracy and sufficiently.

Moreover, in the lens capsule expanding device, it is preferable that the lens capsule expanding device has a bent portion that is formed in the connecting portion so as to be bent in such a manner as to expand in a radially outward direction of the front supporting portion and the rear supporting portion, and a circumferential portion of the optical portion is locked directly or indirectly to the bent portion of the connecting portion, and force is applied directly or indirectly in a radial direction from the connecting portion to the circumferential portion of the optical portion according to movement of the connecting portion when the front supporting portion and the rear supporting portion move in the direction closer to or away from each other with movement of the lens capsule whereby the curvature of the optical portion is changed. According to this configuration, since force is applied directly or indirectly from the connecting portion to the circumferential portion of the optical portion and the curvature of the optical portion changes, it is possible to exert the focus accommodation power with high accuracy and sufficiently.

Moreover, in the lens capsule expanding device, it is preferable that the lens capsule expanding device has a locking member provided on an inner side of the bent portion of the connecting portion, and the circumferential portion of the optical portion is locked to the locking member of the bent portion of the connecting portion. According to this configuration, it is possible to reliably lock the circumferential portion of the optical portion to the connecting portion and to stably arrange the optical portion inside the lens capsule expanding device.

Moreover, it is preferable that the locking member is formed in a U or V-shape that is open in a radially inward direction of the optical portion so as to lock the circumferential portion of the optical portion by sandwiching the circumferential portion from a front-back direction. According to this configuration, even when the optical portion is formed of a soft member which is elastically deformable, it is possible to reliably lock the circumferential portion of the optical portion.

Moreover, the locking member may have a bulging portion that is formed in a front end and/or a rear end so as to swell toward an inner side. According to this configuration, when the circumferential portion of the optical portion is locked to the locking member, since the bulging portion of the locking member presses the circumferential portion of the optical portion toward the inner side so that the central portion of the optical portion swells, the curvature of the optical portion can be changed more effectively.

Moreover, the locking member may lock the circumferential portion of the optical portion in such a manner as to press the circumferential portion from the radial direction. According to this configuration, even when the optical portion is formed of a relatively rigid member which is elastically deformable, it is possible to reliably lock the circumferential portion of the optical portion.

Moreover, the locking member may be formed in a rod shape that extends in a radially inward direction of the optical portion so as to lock the circumferential portion of the optical portion while pressing the circumferential portion in the radially inward direction. According to this configuration, when force is applied directly or indirectly from the connecting portion in the radial direction, the curvature of the optical portion is likely to change.

Moreover, in the lens capsule expanding device, the bent portion of the connecting portion of the lens capsule expanding device may be formed in a U or V-shape, and the bent portion may lock the circumferential portion of the optical portion by sandwiching the circumferential portion from a front-back direction. According to this configuration, it is possible to reliably lock the circumferential portion of the optical portion to the connecting portion and to stably arrange the optical portion inside the lens capsule expanding device.

Moreover, the lens capsule expanding device may include a first connecting portion that connects outer circumferential portions of the front supporting portion and the rear supporting portion and a second connecting portion that connects inner circumferential portions of the front supporting portion and the rear supporting portion, and the optical portion may be locked directly or indirectly to the second connecting portion. According to this configuration, since the first connecting portion is provided in the outer circumferential portions of the front supporting portion and the rear supporting portion, the first connecting portion extends along the lens capsule and the Zinn's zonules and the lens capsule can have moderate tension effectively. Thus, the movement of the ciliary muscles can be transmitted to the lens capsule effectively. Moreover, since the second connecting portion is provided in the inner circumferential portions of the front supporting portion and the rear supporting portion and the second connecting portion is positioned at the opening edge near the center of the anterior capsule which moves best according to the focus accommodation of the eyes or at the vicinity thereof, the degree of bending of the second connecting portion according to the movement in the front-back direction of the front supporting portion and the rear supporting portion changes greatly, and force can be easily applied directly or indirectly from the second connecting portion to the optical portion. Thus, the curvature of the optical portion can be changed effectively. Further, when the second connecting portion is formed so that the outward bending is weaker than that of the first connecting portion, since the degree of bending of the second connecting portion changes greatly according to the movement of the front supporting portion and the rear supporting portion in the front-back direction, the curvature of the optical portion can be changed greatly.

Moreover, the optical portion may have a reinforcing member, for assisting the deformation of the optical portion. According to this configuration, since the assistant member assists deformation of the optical portion, the curvature of the optical portion can be changed effectively.

Moreover, the reinforcing member may include a plurality of U or V-shaped reinforcing members which is elastically deformable in the front-back direction of the optical portion and which is provided at equal intervals along the circumferential portion of the optical portion in such a manner as to sandwich the circumferential portion from the front-back direction. According to this configuration, when force is applied directly or indirectly from the connecting portion of the lens capsule expanding device to the optical portion, since the U-shaped reinforcing member is open or closed whereby the circumferential portion of the optical portion is deformed, the curvature of the optical portion can be changed effectively.

Moreover, the reinforcing member may further include a front reinforcing ring member provided on a front outer surface of the optical portion and a rear reinforcing ring member provided on a rear outer surface of the optical portion, and the front reinforcing ring member and the rear reinforcing ring member may be connected by the plurality of U or V-shaped reinforcing members provided on the circumferential portion of the optical portion. According to this configuration, since the circumferential portion of the optical portion is deformed more reliably when the U or V-shaped reinforcing member is stably open or closed, the curvature of the optical portion can be changed more effectively.

Moreover, the optical portion may be formed of an elastic film which can be expanded and contracted and has a predetermined thickness, and a flowable substance may be filled in the elastic film. According to this configuration, since the optical portion can be easily elastically deformed when force is applied directly or indirectly from the connecting portion to the optical portion, it is possible to effectively change the curvature of the optical portion.

Moreover, the circumferential portion of the optical portion may have a thickness of 20 to 100 μm, a central portion of the optical portion may have a thickness of 5 to 20 μm, and the circumferential portion may be thicker than the central portion. Particularly, it is preferable that the optical portion is formed so that the thickness of the elastic film gradually increases as it advances from the central portion toward the circumferential portion. According to this configuration, a local deformation of the circumferential portion of the optical portion decreases, and the circumferential portion is likely to be deformed generally uniformly. As a result, the central portion of the optical portion is also likely to be deformed uniformly. Moreover, since the central portion of the optical portion is likely to be deformed due to a small thickness, the curvature of the optical portion can be changed effectively.

Moreover, thick portions in which the elastic film of the optical portion is thick may be formed at predetermined intervals along the circumferential portion. According to this configuration, a local deformation of the circumferential portion of the optical portion decreases, and the circumferential portion is likely to be deformed generally uniformly. As a result, since the central portion of the optical portion is also likely to be deformed uniformly, the optical quality of the optical portion is improved and the curvature of the optical portion can be changed effectively.

Moreover, the optical portion may have a bulging portion formed at a front end and/or a rear end of the thick portion of the elastic film so as to swell toward an inner side. According to this configuration, when the optical portion is deformed, the circumferential portion of the optical portion is easily constricted near the bulging portion. As a result, since the central portion of the optical portion is likely to swell, the curvature of the optical portion can be changed effectively.

Moreover, the optical portion may be formed so that a refractive index of the flowable substance gradually increases toward the center of the optical portion. For example, the optical portion may be partitioned in the front-back direction and a segment including the center of the optical portion may have a larger refractive index than the refractive indices of the other segments. According to this configuration, since the closer to the center, the larger the refractive index like a human lens, it is possible to create a large change in the refractive index by a small deformation of the optical portion.

Moreover, the optical portion may have a core member formed at the center and having a larger rigidity than the flowable substance. According to this configuration, when the optical portion applies force directly or indirectly from the connecting portion, since the flowable substance present around the core substance applies force to the elastic film efficiently, the curvature of the optical portion can be changed efficiently.

Moreover, the core member may be a convex lens having a refractive power corresponding to a symptom of a patient. According to this configuration, the optical portion can be used for the purpose of obtaining the accommodation power mainly, and the convex lens provided in the optical portion can be used for the purpose of obtaining a refractive power corresponding to the symptom of a patient. Moreover, it is possible to reduce a refraction error (a difference between a target refractive value before surgery and an actual refractive value after surgery) of the refractive power after surgery.

Moreover, the optical portion may have an injector for injecting the flowable substance into the optical portion. According to this configuration, after the optical portion is folded and inserted into the lens capsule expanding device in a state in which no or a small amount of the flowable substance is present in the optical portion, since the flowable substance can be injected into the optical portion through the injector, it is possible to reduce the size of an incised wound for inserting the accommodating intraocular lens into the lens capsule. Moreover, the refractive power after surgery can be easily adjusted to a target refractive power by injecting or sucking the flowable substance from the injector when a refraction error occurs after surgery.

The lens capsule expanding device may have a convex lens or a concave lens provided in the rear supporting portion and having a refractive power corresponding to a symptom of a patient. According to this configuration, the optical portion can be used for the purpose of obtaining the accommodation power mainly, and the convex lens or the concave lens provided in the rear supporting portion can be used for the purpose of obtaining a refractive power corresponding to the symptom of a patient. Due to this, the optical portion which is elastically deformable is easily folded when it is formed in a flat shape and can be inserted into the eye from a small incised wound of the lens capsule. Moreover, since the convex lens or the concave lens provided in the rear supporting portion supplements the refractive power after surgery mainly, it is possible to reduce a refraction error (a difference between a target refractive value before surgery and an actual refractive value after surgery) of the refractive power after surgery.

Effects of the Invention

According to the present invention, due to the biasing force of the connecting portion, the front supporting portion presses the inner surface of the anterior capsule and the rear supporting portion presses the inner surface of the posterior capsule. As a result, the peripheral portion of the lens equator tries to extend and expand in the front-back direction and the lens equator expands. At the same time, the lens equator moves centripetally and the diameter of the lens equator decreases. Due to this, the Zinn's zonules are pulled in both directions toward the lens capsule and the ciliary bodies and tension of moderate strength is continuously applied to the Zinn's zonules. As a result, moderate tension is applied to the lens capsule. Thus, the Zinn's zonules can transmit the slight contraction and relaxation of the ciliary muscles of the ciliary bodies to the lens capsule with high accuracy, and accordingly, the accommodation function of the optical portion disposed therein can be exerted with high accuracy.

Moreover, when the front supporting portion is formed in an open state like a ring form, hydatoid flows from an anterior capsule incision portion to the space between the front supporting portion and the connecting portion and flows into the lens capsule, and the lens equator is exposed to the hydatoid. Thus, the growth or fibroplasia of the lens epithelial cells in the lens equator is suppressed and the occurrence of the secondary cataract can be prevented.

Further, when the front supporting portion and the rear supporting portion move in the direction closer to or away from each other according to the movement of the lens capsule, force is applied directly or indirectly from the connecting portion according to the movement of the connecting portion and the curvature of the optical portion changes. Thus, it is possible to exert the focus accommodation power with high accuracy and sufficiently.

MODE FOR CARRYING OUT THE INVENTION

First Embodiment

Figure 1:
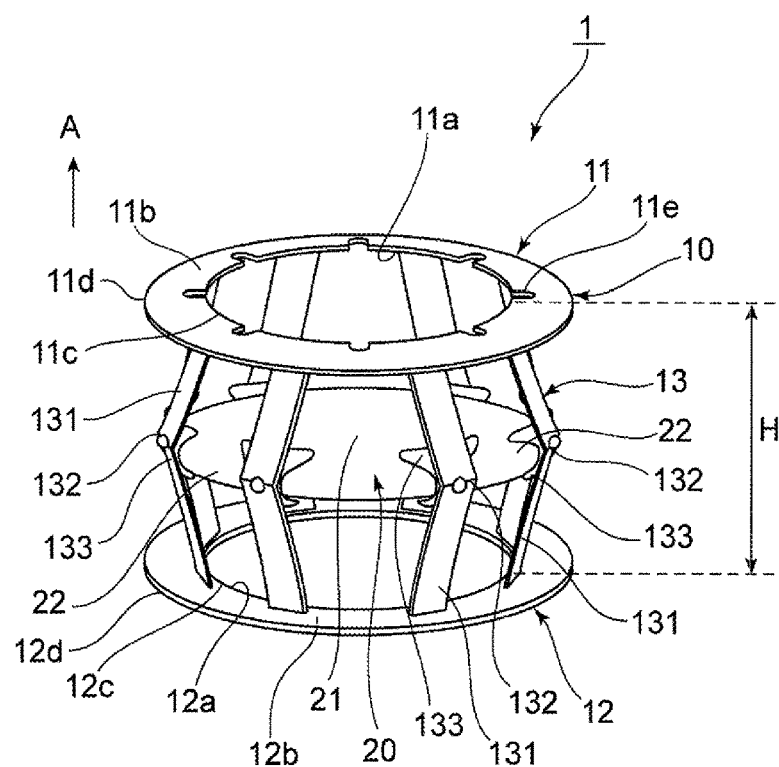
FIG. 1 is a perspective view illustrating an accommodating intraocular lens according to the present invention.

Next, a first embodiment of an accommodating intraocular lens according to the present invention will be described with reference to FIGS. 1 to 5.

An accommodating intraocular lens 1 includes a lens capsule expanding device (hereinafter referred to as a device 10) and an optical portion 20 disposed inside the device 10. In the following description, the direction indicated by arrow A illustrated in the drawings is defined as a front side and the opposite direction is defined as a rear side.

[Device Configuration]

As illustrated in FIG. 5, the device 10 is arranged in the lens capsule S of which the anterior capsule Sf is incised during ophthalmic surgeries such as an extracapsular extraction surgery performed as a part of a cataract surgery, a refractive correction surgery, or a presbyopia correction surgery. As illustrated in FIG. 1, the device 10 includes a front supporting portion 11 positioned on the front side in the lens capsule S, a rear supporting portion 12 positioned on the rear side in the lens capsule S, and a connecting portion 13 that connects the front supporting portion 11 and the rear supporting portion 12.

Figure 2:
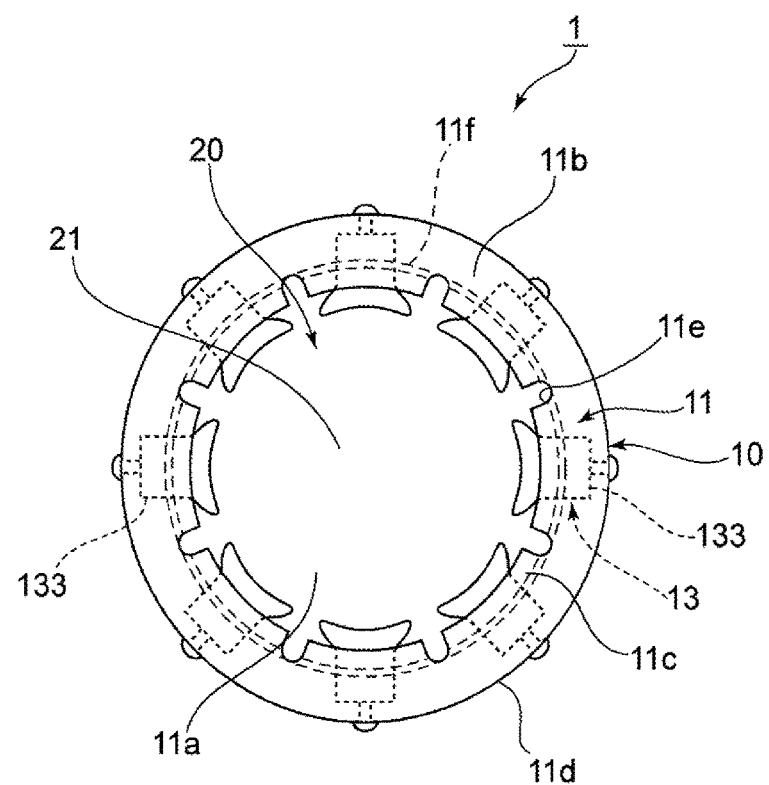
FIG. 2 is a plan view of the accommodating intraocular lens illustrated in FIG. 1.
Figure 3:
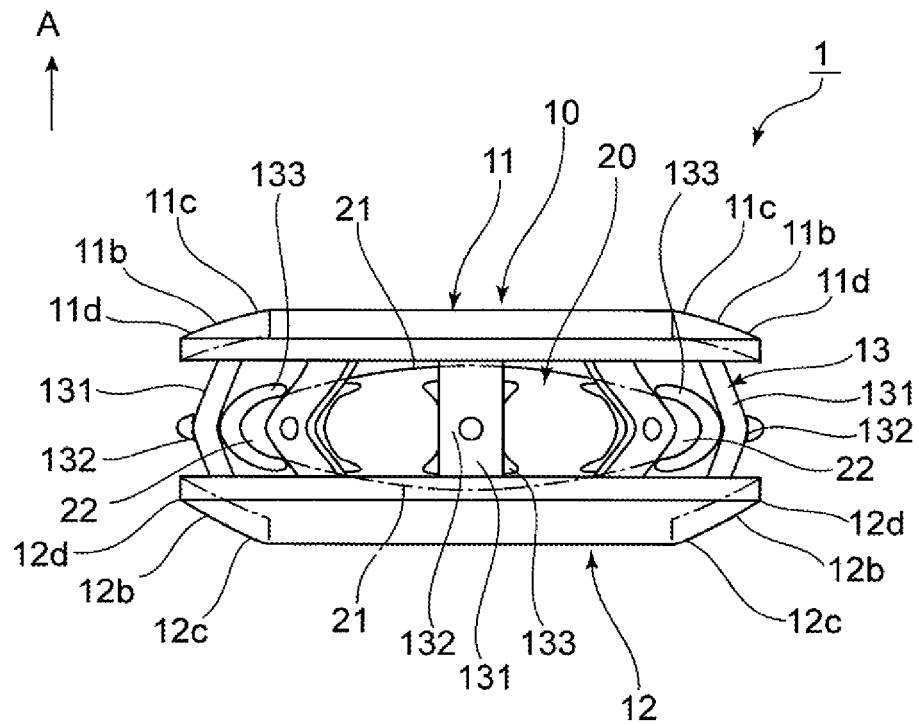
FIG. 3 is a side view of the accommodating intraocular lens illustrated in FIG. 1.

As illustrated in FIGS. 1 and 2, the front supporting portion 11 is a ring-shaped elastic member having an opening 11a at the center. As illustrated in FIG. 3, the front supporting portion 11 has an inclined surface 11b disposed on the front surface side so as to be gradually inclined toward the rear side as it advances from an inner circumferential portion toward an outer circumferential portion. Due to this, as illustrated in FIG. 5, since the front supporting portion 11 is provided in such a manner as to make contact with the inner surface of the anterior capsule Sf of the lens capsule S during a cataract surgery or the like, the inclined surface 11b can reduce the contact load on the anterior capsule Sf when the front supporting portion 11 makes contact with the anterior capsule Sf. Moreover, since the front supporting portion 11 is formed of an elastic material, the front supporting portion 11 is slightly deformed by the force received from the anterior capsule Sf and the contact load between the front supporting portion 11 and the anterior capsule Sf can be reduced further.

Moreover, since a general lens has a diameter of approximately 9 to 10 mm and a thickness of approximately 3.5 to 5.5 mm, the front supporting portion 11 is formed such that an outer circumferential portion 11d has a diameter of 7.0 mm, the opening 11a (an inner circumferential portion 11c) has a diameter of 5.0 mm, and the inclined surface 11b making contact with the anterior capsule Sf has a width of 1.5 mm and a thickness of 0.2 to 0.5 mm.

Moreover, as illustrated in FIG. 2, radial notches 11e are formed in the front supporting portion 11 so as to extend from the inner circumferential portion 11c toward the outer circumferential portion 11d. When the notches 11e are formed in such a manner, the inner circumferential portion 11c of the front supporting portion 11 can move a large distance in the front-back direction, a change in the degree of bending of bent portions 132 of the connecting portion 13 is large. Thus, the curvature of a central portion 21 of the optical portion 21 can be changed effectively. When a groove 11f is formed in a front or a rear surface of the front supporting portion 11 in such a manner as to connect the distal ends of the notches 11e, a change in the degree of bending of the bent portions 132 of the connecting portion 13 can be increased.

Figure 4:
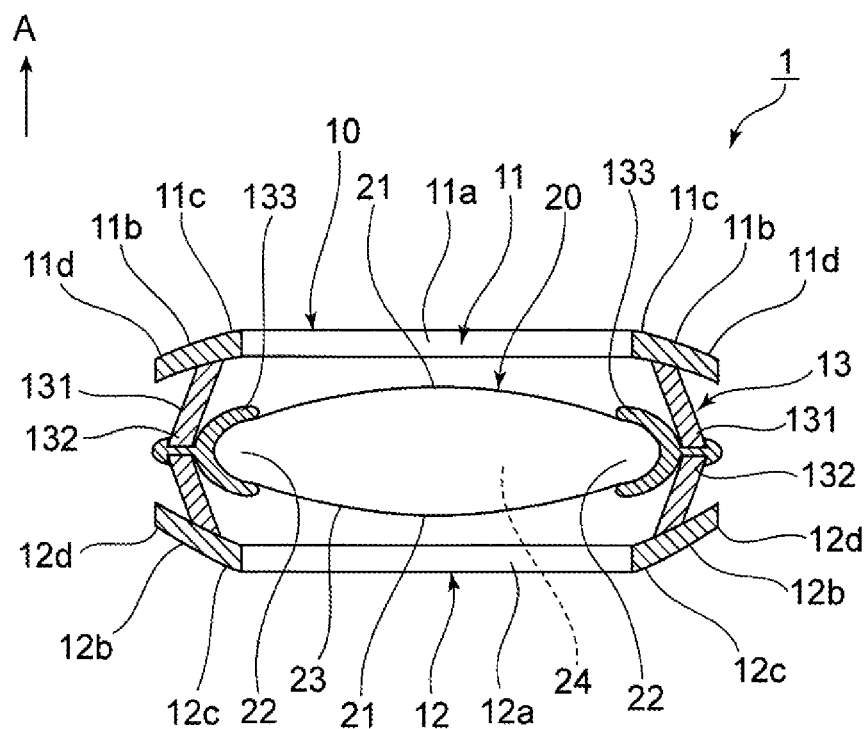
FIG. 4 is a longitudinal cross-sectional view of the accommodating intraocular lens illustrated in FIG. 1.

The rear supporting portion 12 is a ring-shaped elastic member having an opening 12a at the center similarly to the front supporting portion 11 and is disposed on the rear side of the front supporting portion 11 in such a manner as to face the front supporting portion 11 in parallel. As illustrated in FIG. 4, the rear supporting portion 12 has an inclined surface 12b disposed on the rear surface side so as to be gradually inclined toward the front side as it advances from an inner circumferential portion 12c toward an outer circumferential portion 12d. Due to this, as illustrated in FIG. 5, since the rear supporting portion 12 is provided in such a manner as to make contact with the inner surface of the posterior capsule Sb of the lens capsule S of the lens capsule S, the inclined surface 12b can reduce the contact load on the posterior capsule Sb when the rear supporting portion 12 makes contact with the posterior capsule Sb. Moreover, since the rear supporting portion 12 is formed of an elastic material, the rear supporting portion 12 is slightly deformed by the force received from the posterior capsule Sb and the contact load between the rear supporting portion 12 and the posterior capsule Sb can be reduced further. Moreover, the thickness of the rear supporting portion 12 preferably decreases gradually as it advances from the inner circumferential portion toward the outer circumferential portion.

Moreover, the rear supporting portion 12 is formed based on the size of a general lens such that, as illustrated in FIG. 4, an outer circumferential portion 12d has a diameter of 7.0 mm, an opening 12a (an inner circumferential portion 12c) has a diameter of 5.0 mm, and the inclined surface 12b making contact with the posterior capsule Sb has a width of 1.5 mm and a thickness of 0.6 mm to 0.2 mm as it advances from the inner circumferential portion toward the outer circumferential portion. When the width of the rear supporting portion 12 is set to be larger than the width of the front supporting portion 11 in this manner, since the contact area between the rear supporting portion 12 and the posterior capsule Sb is larger than the contact area between the front supporting portion 11 and the anterior capsule Sf, the rear supporting portion 12 can be arranged stably in the lens capsule S.

As illustrated in FIG. 1, the connecting portion 13 includes eight connecting pieces 131 provided at equal intervals in the circumferential direction of the front supporting portion 11 and the rear supporting portion 12. This connecting piece 131 is a thin plate member formed of an elastic material such as a synthetic resin. One end of the connecting piece 131 is fixed to the rear surface of the front supporting portion 11 in such a manner as to extend in an orthogonal direction or a slightly radially outward direction, and the other end is fixed to the front surface of the rear supporting portion 12 in such a manner as to extend in an orthogonal direction or a slightly radially outward direction.

Moreover, in a natural state in which the connecting piece 131 is not elastically deformed, the connecting portion 13 connects the front supporting portion 11 and the rear supporting portion 12 at a predetermined interval H. This predetermined interval H is such a length that the connecting piece 131 is slightly bent when this device 1 is arranged in the lens capsule S. Moreover, when the front supporting portion 11 and the rear supporting portion 12 are moved in a direction closer to each other, the connecting portion 13 is bent in such a manner as to expand in a radially outward direction of the front supporting portion 11 and the rear supporting portion 12. Due to this, when the device 10 is arranged in the lens capsule S, a state in which the connecting piece 131 is bent in a radially outward direction is created and elastic force to restore to an original shape is generated. Thus, it is possible to create a state in which the connecting portion 13 applies biasing force in a direction of separating the front supporting portion 11 and the rear supporting portion 12 from each other using the generated elastic force. Moreover, due to the biasing force of the plurality of connecting pieces 131, the connecting portion 13 can extend and expand the anterior capsule Sf and the posterior capsule Sb in the front-back direction efficiently in the entire circumference to open the lens equator Se and applies tension of moderate strength to the Zinn's zonules Z and the lens capsule S.

Moreover, the length and the biasing force of the connecting portion 13 are accommodated so as to have the biasing force corresponding to the tension of the Zinn's zonules Z and the lens capsule S generated during contraction or relaxation of the ciliary muscles Cm of the ciliary bodies C. Due to this, it is possible to continuously apply tension of more moderate strength to the Zinn's zonules Z and the lens capsule S when the device 10 is arranged in the lens capsule S.

Moreover, as illustrated in FIG. 3, the connecting portion 13 connects the inner circumferential portion 11c of the front supporting portion 11 and the inner circumferential portion 12c of the rear supporting portion 12. Due to this, since the connecting portion 13 is positioned at the opening edge near the center of the anterior capsule Sf which moves best according to the focus accommodation of the eyes or at the vicinity thereof, it is possible to increase the degree of change in bending of the connecting portion 13 according to the movement of the anterior capsule Sf due to the contraction and relaxation of the ciliary muscles by the focus accommodation. Further, it is possible to effectively change the curvature of the central portion 21 of the optical portion 20 according to the curvature of the connecting portion 13.

Moreover, as illustrated in FIG. 4, a bent portion 132 for bending the connecting piece 131 in such a manner as to expand in a radially outward direction of the front supporting portion 11 and the rear supporting portion 12 is formed in advance in the connecting portion 13. Due to this, when the front supporting portion 11 and the rear supporting portion 12 move in a direction closer to each other as described later, the connecting portion 13 can be reliably bent in such a manner as to expand in the radially outward direction based on the bent portion 132. Further, since the bent portion 132 is bent in a folded manner, the connecting portion 13 can be bent more reliably in such a manner of expanding in the radially outward direction based on the folded bent portion 132.

Moreover, as illustrated in FIG. 4, the connecting portion 13 has a locking member 133 on the inner side of each bent portion 132. This locking member 133 is formed in a U or V-shape that is open to the inner side in the radial direction of the optical portion 20 so as to hold and lock a circumferential portion 22 of the optical portion 22 in the valley portion of the U or V-shape by sandwiching the circumferential portion 22 of the optical portion 20 from the front-back direction. According to this configuration, even when the optical portion 20 is formed of a soft member which is elastically deformable, it is possible to reliably lock the circumferential portion 22 of the optical portion 20. When the locking member 133 locks the circumferential portion 22 of the optical portion 20, a gap may be formed between the locking member 133 and the circumferential portion 22 of the optical portion 20.

When the degree of expansion in the radially outward direction of the connecting portion 13 increases with movement of the front supporting portion 11 and the rear supporting portion 12 in the direction closer to each other, these locking members 133 move in a direction away from each other in the radial direction and the distance between the locking members 133 increases. Moreover, when the degree of expansion in the radially outward direction of the connecting portion 13 decreases with movement of the front supporting portion 11 and the rear supporting portion 12 in the direction away from each other, the locking members 133 move in the direction closer to each other in the radial direction and the distance between the locking members 133 decreases.

[Configuration of Optical Portion]

The optical portion 20 is a flat convex lens formed of an elastic film having a thickness of 5 to 100 μm and a flowable substance 24 is filled therein. The optical portion 20 includes the central portion 21 positioned at the center of the optical portion 20 to refract light and the circumferential portion 22 positioned at the circumference of the optical portion 20.

The optical portion 20 is formed of a material having the same elasticity as the lens of a young person, such as silicon polymer, acrylic polymer, temperature-responsive shape-memory hydrophobic acryl, hydroxyethyl methacrylate, photo-curable resins, or hydrogel. According to this configuration, since the optical portion 20 can be easily elastically deformed when force is applied directly or indirectly from the connecting portion 13 to the optical portion 20, it is possible to effectively change the curvature of the optical portion 20.

The central portion 21 is a portion which is positioned at the center of the optical portion 20 and has a function of refracting light to accommodate the focus. During distance vision (non-accommodation), since the circumferential portion 22 of the optical portion is not pressed in the radially inward direction by the connecting pieces 131 of the connecting portion 13, the central portion 21 is relaxed up to the original shape of the optical portion 20 and the curvature thereof decreases. During near vision (during focus accommodation), when the circumferential portion 22 of the optical portion 20 is pressed in the radially inward direction by the connecting pieces 131 of the connecting portion 13, the central portion 21 is elastically deformed in such a manner as to inflate in the thickness direction of the optical portion 20 and the curvature thereof increases.

Moreover, the circumferential portion 22 is positioned at the circumference of the optical portion 20 and is locked by the U or V-shaped locking member 133 provided in the device 10. According to this configuration, since the circumferential portion 22 is reliably locked to the connecting portion 13 by the locking members 133, it is possible to arrange the optical portion 20 inside the device 1. Moreover, force can be easily applied from the connecting portion 13 to the circumferential portion 22 of the optical portion 20 in the radial direction, and the curvature of the optical portion 20 can be effectively deformed.

[Implantation of Accommodating Intraocular Lens]

Next, implantation of the accommodating intraocular lens 1 will be described with reference to FIG. 5.

First, when the optical portion 20 is housed inside the device 10, the optical portion 20 is inserted from the openings 11a or 12a of the front supporting portion 11 or the rear supporting portion 12 of the device 10, and then, the circumferential portion 22 of the optical portion 20 is locked to the locking member 133 of each connecting piece 131 of the connecting portion 13. In this way, the optical portion 20 is housed in such a manner that the optical portion 20 is surrounded by the connecting pieces 131 of the connecting portion 13 between the front supporting portion 11 and the rear supporting portion 12 and is parallel to the front supporting portion 11 and the rear supporting portion 12.

Figure 5A:
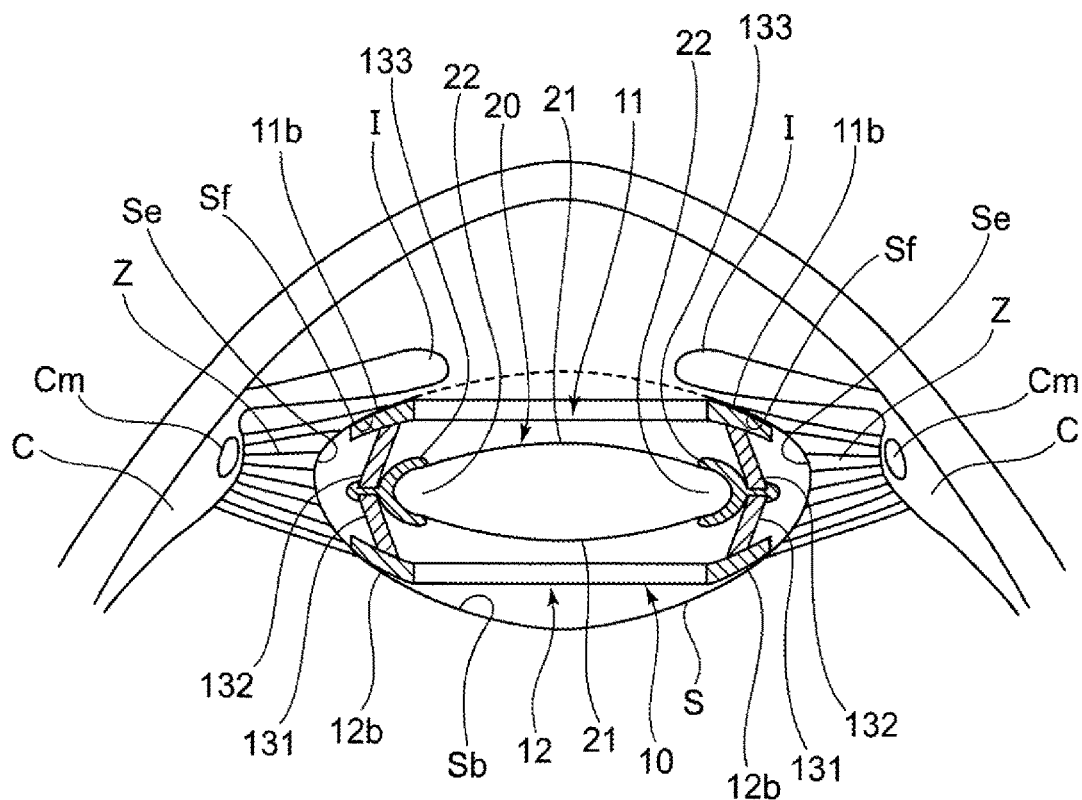
FIG. 5(a) is a side view illustrating the movement during focus accommodation, of the accommodating intraocular lens illustrated in FIG. 1 inserted into the eye.

Subsequently, when the accommodating intraocular lens 1 is implanted in the lens capsule S, as illustrated in FIG. 5(a), the accommodating intraocular lens 1 is inserted into the lens capsule S from a portion in which the anterior capsule Sf is incised during a cataract surgery or the like and the accommodating intraocular lens 1 is implanted in the lens capsule S in a parallel state in such a manner that the front supporting portion 11 makes contact with the inner surface of the anterior capsule Sf and the rear supporting portion 12 makes contact with the inner surface of the posterior capsule Sb. In this case, since the distance H between the front supporting portion 11 and the rear supporting portion 12 is larger than the distance between the anterior capsule Sf and the posterior capsule Sb, the front supporting portion 11 and the rear supporting portion 12 move in the direction closer to each other while being pressed by the anterior capsule Sf and the posterior capsule Sb. Due to this, a state in which the connecting pieces 131 are bent in such a manner as to expand in the radially outward direction based on the bent portion 132 is created and the biasing force of the connecting pieces 131 is generated. Due to the biasing force, the front supporting portion 11 presses the inner surface of the anterior capsule Sf and the rear supporting portion 12 presses the inner surface of the posterior capsule Sb. In order to apply tension of moderate strength corresponding to the contraction and relaxation of the ciliary muscles Cm of the ciliary bodies C to the lens capsule S (the anterior capsule Sf and the posterior capsule Sb), it is preferable to implant the accommodating intraocular lens 1 (the lens capsule expanding device 10) having a height corresponding to the thickness of the lens measured by ultrasound scanning before surgery.

Thus, due to the biasing force of the connecting portion 13, the front supporting portion 11 presses the inner surface of the anterior capsule and the rear supporting portion 12 presses the inner surface of the posterior capsule. As a result, the peripheral portion of the lens equator Se tries to extend and expand in the front-back direction and the lens equator Se expands. At the same time, the lens equator Se moves centripetally and the diameter of the lens equator Se decreases. Due to this, the Zinn's zonules Z are pulled in both directions toward the lens capsule S and the ciliary bodies C and tension of moderate strength is continuously applied to the Zinn's zonules Z. As a result, tension of moderate strength is generated in the lens capsule S (the anterior capsule Sf and the posterior capsule Sb). Thus, the Zinn's zonules Z can transmit the slight contraction and relaxation of the ciliary muscles Cm of the ciliary bodies C to the lens capsule S with high accuracy, and accordingly, the accommodation function of the optical portion 20 disposed therein can be exerted with high accuracy.

In the present embodiment, although a case in which the optical portion 20 is disposed integrally in the device 10 when the device 10 is implanted in the lens capsule S has been described, the optical portion 20 may be arranged in the device 10 after the device 10 is implanted in the lens capsule S. During implantation of the device 10, the device 10 may be folded and mounted on an injector and be inserted into the lens capsule S or the device 10 may be folded by tweezers and be inserted into the lens capsule S.

[Focus Accommodation Function of Accommodating Intraocular Lens]

Next, the focus accommodation function of the accommodating intraocular lens 1 implanted in the lens capsule S will be described.

As illustrated in FIG. 5(a), during distance vision (non-accommodation), the ciliary muscles Cm of the ciliary bodies C are relaxed to have a flat shape and the ciliary bodies C are retracted in a direction away from the lens capsule S. Moreover, the peripheral portion of the lens equator Se is pulled in the radially outward direction by the tension of the Zinn's zonules Z which continuously have tension of moderate strength due to the accommodating intraocular lens 1 implanted in the lens capsule S. Due to this, since the lens capsule S is deformed so that the thickness of the lens capsule S decreases, the distance between the anterior capsule Sf and the posterior capsule Sb decreases and the front supporting portion 11 and the rear supporting portion 12 move in the direction closer to each other. As a result, a state in which the connecting pieces 131 are bent in such a manner as to expand in the radially outward direction based on the bent portion 132 is created and the biasing force of the connecting pieces 131 is generated. Due to the biasing force, the front supporting portion 11 presses the inner surface of the anterior capsule Sf, and the rear supporting portion 12 presses the inner surface of the posterior capsule Sb to create a state in which equilibrium with the tension of the Zinn's zonules Z is maintained.

In this case, since the degree of expansion of the connecting portion 13 in the radially outward direction increases, the locking members 133 of the connecting pieces 131 move in the direction away from each other and the distance between the facing locking members 133 increases. Thus, the optical portion 20 does not receive force in the radially inward direction from the connecting pieces 131 of the connecting portion 13 and is relaxed up to the original shape whereby the curvature of the central portion 21 decreases. In this manner, the accommodation function of the optical portion 20 during distance vision can be exerted according to the relaxation of the ciliary muscles Cm of the ciliary bodies C.

Figure 5B:
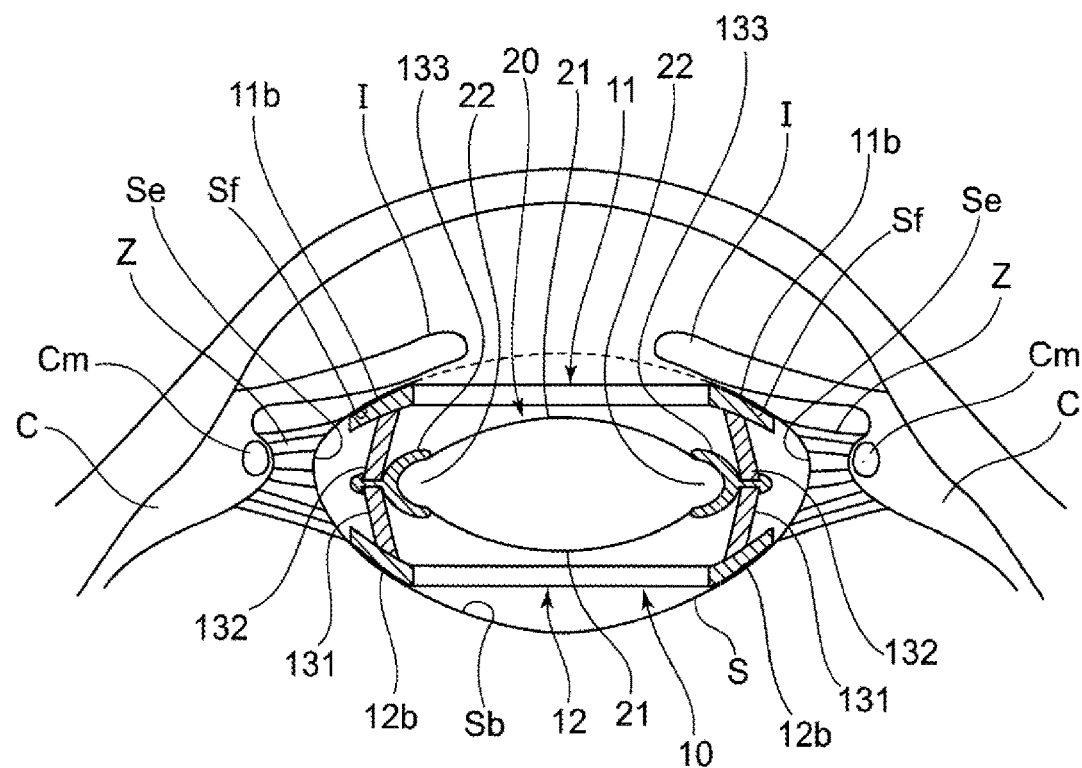
FIG. 5(b) is a side view illustrating the movement during focus accommodation, of the accommodating intraocular lens illustrated in FIG. 1 inserted into the eye.

On the other hand, during near vision (focus accommodation), as illustrated in FIG. 5(b), the ciliary muscles Cm of the ciliary bodies C are contracted to protrude centripetally (toward the lens capsule S), and the degree of tension of the Zinn's zonules Z decreases. As a result, since the tension of the peripheral portion of the lens equator Se decreases, the front supporting portion 11 and the rear supporting portion 12 are biased by the biasing force of the connecting portion 13 and are moved in a direction away from each other while resisting the tension of the Zinn's zonules Z.

In this case, since the connecting pieces 131 are elastically deformed to restore to the natural state and the degree of bending of the connecting portion 13 in the radially outward direction decreases, the locking members 133 move in the direction closer to each other and the distance between the facing locking members 133 decreases. Thus, the circumferential portion 22 of the optical portion 20 is pressed in the radially inward direction by the locking members 133 from the connecting pieces 131 of the connecting portion 13 and the central portion 21 is elastically deformed in such a manner as to inflate in the thickness direction whereby the curvature of the central portion 21 increases. In this manner, the accommodation function of the optical portion 20 during near vision can be exerted according to the contraction of the ciliary muscles Cm of the ciliary bodies C.

In this way, in the accommodating intraocular lens 1, the Zinn's zonules Z can transmit the slight contraction and relaxation of the ciliary muscles Cm of the ciliary body C with high accuracy due to the structure of the device 10, and accordingly, the accommodation function of the optical portion 20 can be exerted with high accuracy.

Moreover, in the accommodating intraocular lens 1, when the front supporting portion 11 is formed in an open state like a ring form, hydatoid flows from an anterior capsule incision portion to the space between the front supporting portion and the connecting portion and flows into the lens capsule, and the lens equator Se is exposed to the hydatoid. Thus, the growth or fibroplasia of the lens epithelial cells in the lens equator Se is suppressed and the occurrence of the secondary cataract can be prevented. In particular, in the present embodiment, since the hydatoid enters from the opening 11a which is open in a ring form and flows reliably into the lens equator Se from the space between the connecting pieces 131, it is possible to reliably suppress the growth or fibroplasia of the lens epithelial cells in the lens equator Se.

Further, in the accommodating intraocular lens 1, when the front supporting portion 11 and the rear supporting portion 12 move in the direction closer to or away from each other according to the movement of the lens capsule S, force is applied directly or indirectly from the connecting portion 13 according to the movement of the connecting portion 13 and the curvature of the optical portion 20 changes. Thus, it is possible to exert the focus accommodation power with high accuracy and sufficiently.

Second Embodiment

Next, a second embodiment of the accommodating intraocular lens 1 according to the present invention will be described with reference to FIG. 6. In the following description, only constituent elements different from those of the above-described embodiment will be described and the same constituent elements as those of the above-described embodiment will be denoted by the same reference numerals and the description thereof will be omitted.

In the device 10 according to the present embodiment, as illustrated in FIG. 6, the locking member 133 is not provided, and the circumferential portion 22 of the optical portion 20 is directly locked to the inner side of the connecting pieces 131.

Figure 6A:
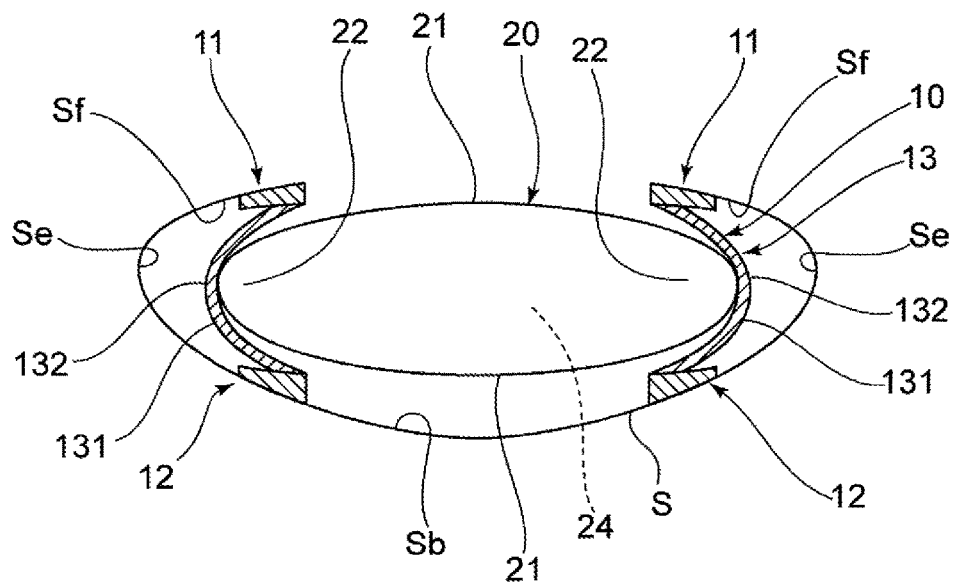
FIG. 6(a) is a longitudinal cross-sectional view of an accommodating intraocular lens according to a second embodiment.

Thus, as illustrated in FIG. 6(a), during distance vision (non-focus accommodation), the front supporting portion 11 and the rear supporting portion 12 move in the direction closer to each other and the degree of expansion of the connecting portion 13 in the radially outward direction increases. As a result, the facing connecting pieces 131 move in the direction away from each other and the distance between the connecting pieces 131 increases. Therefore, the optical portion 20 does not receive force in the radially inward direction from the connecting pieces 131 of the connecting portion 13 and is relaxed up to the original shape whereby the curvature of the central portion 21 decreases.

Figure 6B:
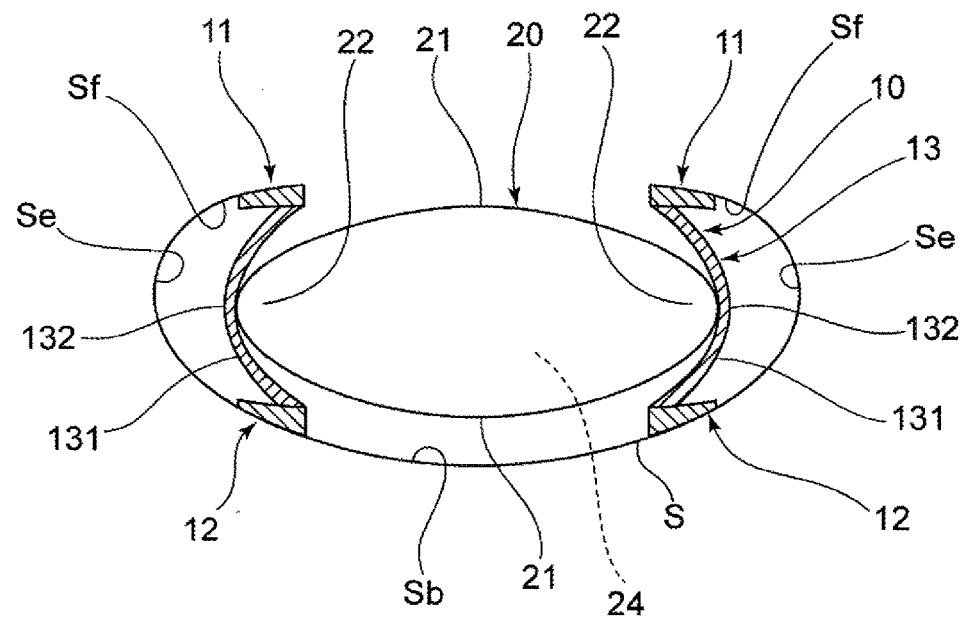
FIG. 6(b) is a longitudinal cross-sectional view of an accommodating intraocular lens according to a second embodiment.

Moreover, as illustrated in FIG. 6(b), during near vision (focus accommodation), the front supporting portion 11 and the rear supporting portion 12 move in the direction away from each other, the connecting pieces 131 of the connecting portion 13 are elastically deformed to restore to the natural state, and the degree of bending of the connecting portion 13 in the radially outward direction decreases. As a result, the facing connecting pieces 131 move in the direction closer to each other and the distance between the connecting pieces 131 decreases. Therefore, the circumferential portion 22 of the optical portion 20 receives force directly from the connecting pieces 131 of the connecting portion 13 and is pressed in the radially inward direction, and the central portion 21 is elastically deformed in such a manner as to inflate in the thickness direction, whereby the curvature of the central portion 21 increases.

Third Embodiment

Next, a third embodiment of the accommodating intraocular lens 1 according to the present invention will be described with reference to FIG. 7.

As illustrated in FIG. 7, the locking member 133 according to the present embodiment has a bulging portion 133a which is formed on the inner side of a front end and a rear end.

Figure 7A:
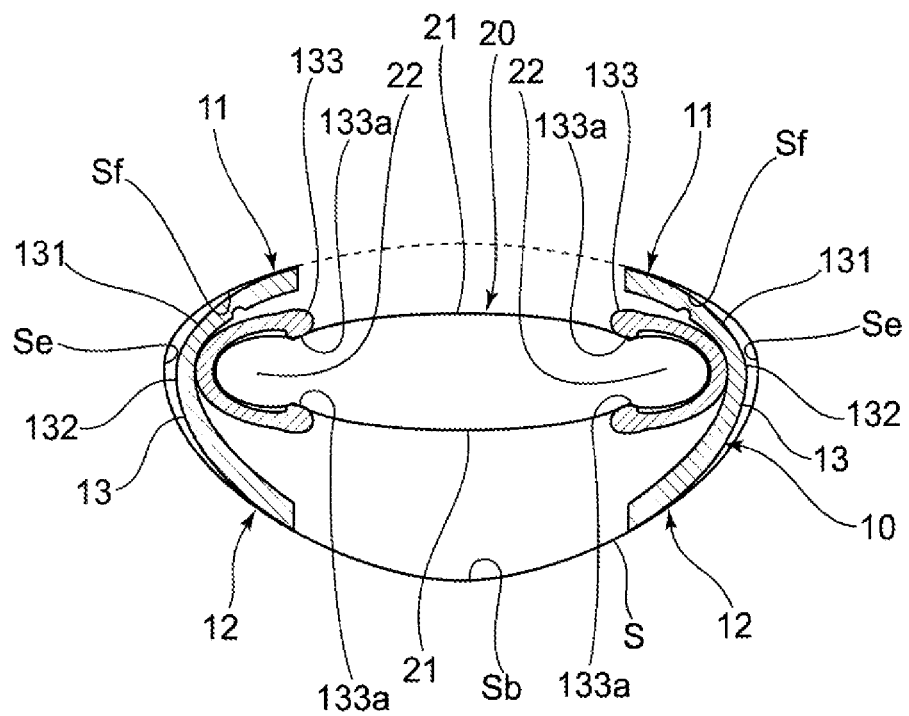
FIG. 7(a) is a longitudinal cross-sectional view of an accommodating intraocular lens according to a third embodiment.

Thus, as illustrated in FIG. 7(a), during distance vision (non-focus accommodation), the front supporting portion 11 and the rear supporting portion 12 move in the direction closer to each other and the degree of expansion of the connecting portion 13 in the radially outward direction increases. As a result, the facing connecting pieces 131 move in the direction away from each other and the distance between the connecting pieces 131 increases. Therefore, the optical portion 20 does not receive force in the radially inward direction from the connecting pieces 131 of the connecting portion 13 and is relaxed up to the original shape whereby the curvature of the central portion 21 decreases.

Figure 7B:
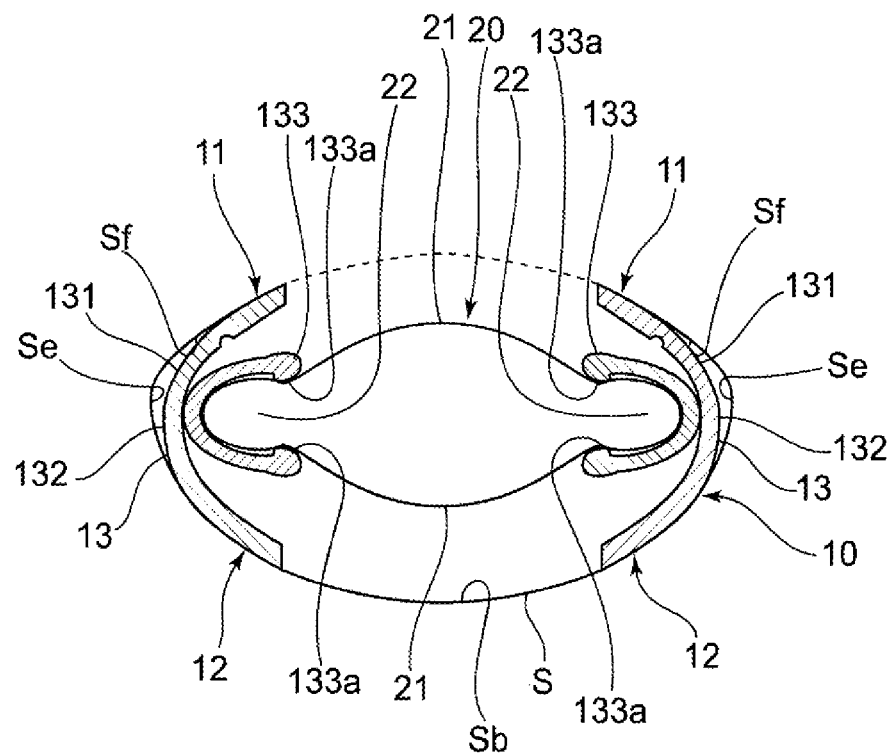
FIG. 7(b) is a longitudinal cross-sectional view of an accommodating intraocular lens according to a third embodiment.

Moreover, as illustrated in FIG. 7(b), during near vision (focus accommodation), the front supporting portion 11 and the rear supporting portion 12 move in the direction away from each other, the connecting pieces 131 of the connecting portion 13 are elastically deformed to restore to the natural state, and the degree of bending of the connecting portion 13 in the radially outward direction decreases. As a result, the facing connecting pieces 131 move in the direction closer to each other and the distance between the connecting pieces 131 decreases. Therefore, the circumferential portion 22 of the optical portion 20 is pressed in the radially inward direction by the locking member 133 from the connecting pieces 131 of the connecting portion 13 and the central portion 21 is elastically deformed in such a manner as to inflate in the thickness direction, whereby the curvature of the central portion 22 increases. In this case, the bulging portion 133a presses the circumferential portion 22 of the optical portion 20 toward the inner side so that the central portions 21 on the front and rear side of the optical portion 20 swell. Thus, the inclination of the optical portion 20 at the circumference of the central portion 21 increases and the curvature of the central portion 21 of the optical portion 20 can be changed more effectively.

The connecting portion 13 according to the present embodiment integrally connects the outer circumferential portion 11d of the front supporting portion 11 and the outer circumferential portion 12d of the rear supporting portion 12. According to this configuration, since the connecting portion 13 extends along the lens capsule S and the Zinn's zonules Z and the lens capsule S can have moderate tension effectively, the movement of the ciliary muscles Cm can be transmitted to the lens capsule S effectively.

Fourth Embodiment

Next, a fourth embodiment of the accommodating intraocular lens 1 according to the present invention will be described with reference to FIG. 8.

Figure 8:
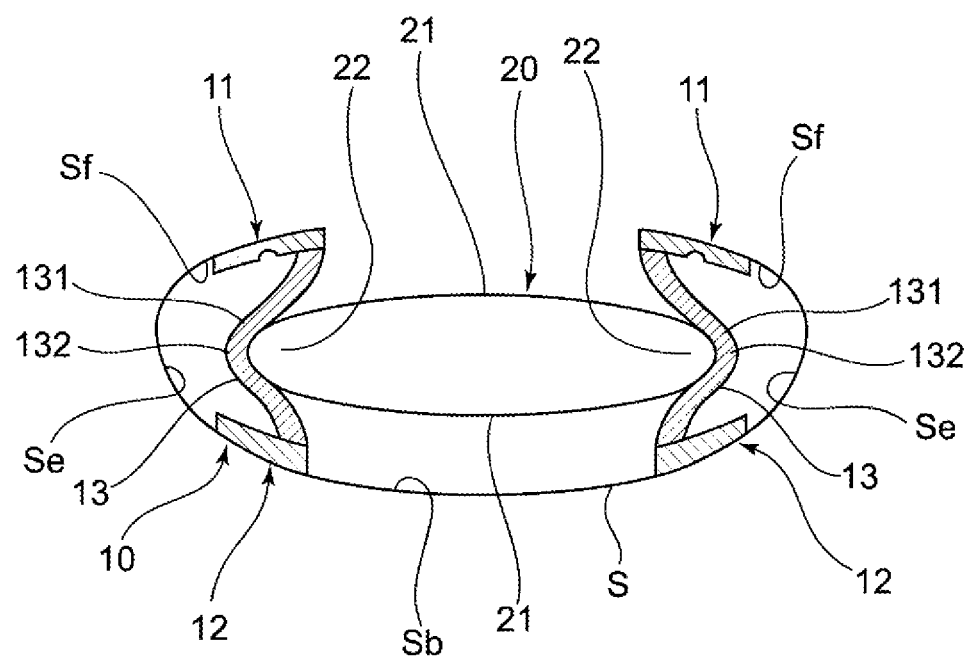
FIG. 8 is a longitudinal cross-sectional view of an accommodating intraocular lens according to a fourth embodiment.

As illustrated in FIG. 8, in the device 10 according to the present embodiment, the bent portion 132 of the connecting portion 13 is formed in a U or V-shape, and the bent portion 132 locks the circumferential portion 22 of the optical portion 20 by sandwiching the circumferential portion 22 from the front-back direction. According to this configuration, it is possible to reliably lock the circumferential portion 22 of the optical portion 20 to the connecting portion 13 and to stably arrange the optical portion 20 inside the device 1.

Fifth Embodiment

Next, a fifth embodiment of the accommodating intraocular lens 1 according to the present invention will be described with reference to FIG. 9.

The connecting portion 13 according to the present embodiment includes a first connecting portion 13a that connects the outer circumferential portions 11d and 12d of the front supporting portion 11 and the rear supporting portion 12 and a second connecting portion 13b that connects the inner circumferential portions 11c and 12c of the front supporting portion 11 and the rear supporting portion 12.

The first connecting portion 13a includes a plurality of connecting pieces 131a provided at equal intervals in the circumferential direction of the front supporting portion 11 and the rear supporting portion 12. This connecting piece 131a is a thin plate member formed of an elastic material such as a synthetic resin. One end of the connecting piece 131 is fixed to the rear surface of the front supporting portion 11 in such a manner as to extend in an orthogonal direction or a slightly radially outward direction, and the other end is fixed to the front surface of the rear supporting portion 12 in such a manner as to extend in an orthogonal direction or a slightly radially outward direction.

According to this configuration, since the first connecting portion 13a is provided in the outer circumferential portions 11d and 12d of the front supporting portion 11 and the rear supporting portion 12, the first connecting portion 13a extends along the lens capsule S and the Zinn's zonules Z and the lens capsule S can have moderate tension effectively. Thus, the movement of the ciliary muscles can be transmitted to the lens capsule S effectively.

On the other hand, the second connecting portion 13b includes a plurality of connecting pieces 131b provided at equal intervals in the circumferential direction of the front supporting portion 11 and the rear supporting portion 12, each connecting piece being disposed between the connecting pieces 131a. The second connecting portion 13b locks the circumferential portion 22 of the optical portion 20 by sandwiching the circumferential portion 22 from the front-back direction with the locking member 133b of the bent portion 132b interposed. This connecting piece 131b is a thin plate member formed of an elastic material such as a synthetic resin similarly to the connecting piece 131a. One end of the connecting piece 131 is fixed to the rear surface of the front supporting portion 11 in such a manner as to extend in an orthogonal direction or a slightly radially outward direction, and the other end is fixed to the front surface of the rear supporting portion 12 in such a manner as to extend in an orthogonal direction or a slightly radially outward direction.

Figure 9A:
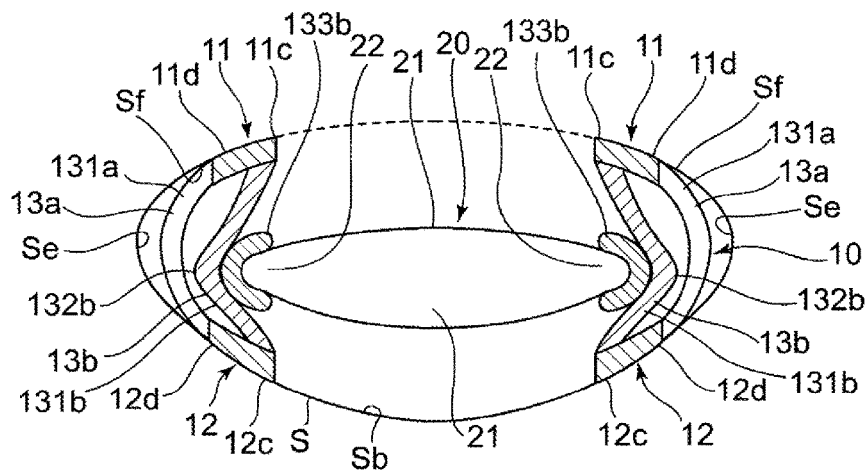
FIG. 9(a) is a longitudinal cross-sectional view of an accommodating intraocular lens according to a fifth embodiment.
Figure 9B:
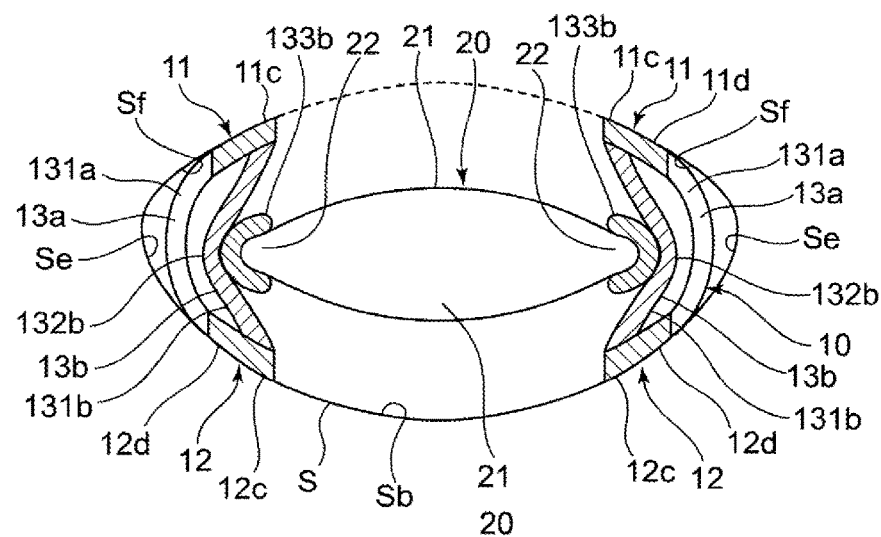
FIG. 9(b) is a longitudinal cross-sectional view of an accommodating intraocular lens according to a fifth embodiment.
Figure 9C:
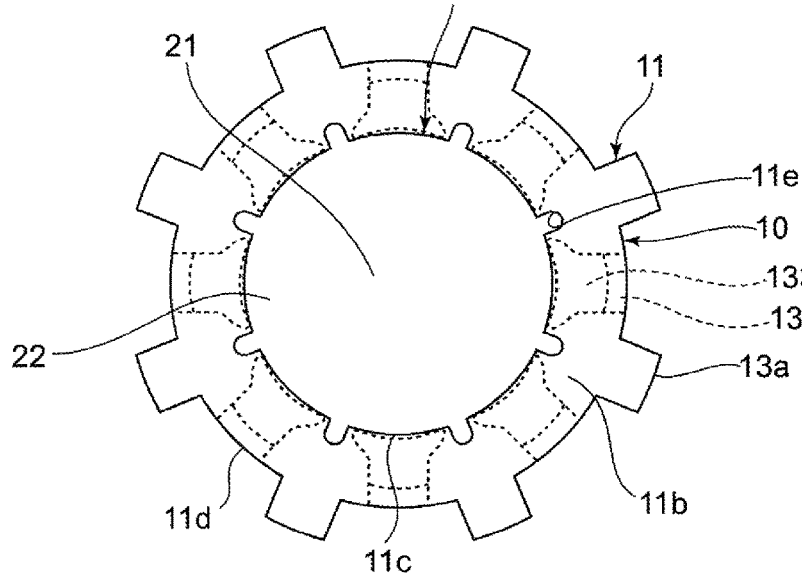
FIG. 9(c) shows a front supporting portion and rear supporting portion of an accommodating intraocular lens according to a fifth embodiment.

Moreover, as illustrated in FIGS. 9(a) and 9(b), the second connecting portion 13b connects the inner circumferential portion 11c of the front supporting portion 11 and the inner circumferential portion 12c of the rear supporting portion 12. Due to this, since the second connecting portion 13b is positioned at the opening edge near the center of the anterior capsule Sf which moves best according to the focus accommodation of the eyes or at the vicinity thereof, the degree of bending of the second connecting portion 13b according to the movement in the front-back direction of the front supporting portion 11 and the rear supporting portion 12 changes greatly, and force can be easily applied directly or indirectly from the second connecting portion 13b to the optical portion 20. Thus, the curvature of the optical portion 20 can be changed effectively. Further, when the second connecting portion 13b is formed so that the outward bending is weaker than that of the first connecting portion 13a, since the degree of bending of the second connecting portion 13b changes greatly according to the movement of the front supporting portion 11 and the rear supporting portion 12 in the front-back direction, the curvature of the optical portion 20 can be changed greatly.

Sixth Embodiment

Next, an eighth embodiment of the accommodating intraocular lens 1 according to the present invention will be described with reference to FIG. 10.

In the optical portion 20 according to the present embodiment, a reinforcing member for assisting the deformation of the optical portion 20 is formed in the circumferential portion 22. The reinforcing member 40 includes a plurality of reinforcing members 31 having a U or V-shape, which can be elastically deformed in the front-back direction of the optical portion 20. The reinforcing members 41 are provided at predetermined intervals along the circumferential portion 22 in such a manner as to sandwich the circumferential portion 22 of the optical portion 20.

Thus, as illustrated in FIG. 12(a), during distance vision (non-focus accommodation), when the front supporting portion 11 and the rear supporting portion 12 move in the direction closer to each other and the degree of expansion of the connecting portion 13 in the radially outward direction increases, the bent portions 132 move in the direction away from each other, the distance between both bent portions 132 increases, and the optical portion 20 is relaxed to the original shape. In this case, the circumferential portion 22 closes the U-shaped reinforcing member 41 and is deformed in such a manner that the thickness decreases, whereby the central portion 21 is deformed with high accuracy. Due to this, the optical portion 20 is relaxed in the original shape and the curvature of the central portion 21 of the optical portion 20 can be decreased effectively.

Moreover, as illustrated in FIG. 12(b), during near vision (focus accommodation), when the front supporting portion 11 and the rear supporting portion 12 move in the direction away from each other and the degree of expansion of the connecting portion 13 in the radially outward direction decreases, the connecting pieces 131 move in the direction closer to each other, the distance between both bent portions 132 decreases, and the circumferential portion 22 is pressed in the radially inward direction. In this case, the circumferential portion 22 opens the U-shaped reinforcing member 41 and is deformed in such a manner that the thickness thereof increases, and the central portion 21 is deformed with high accuracy. Due to this, it is possible to effectively increase the curvature of the central portion 21 of the optical portion 20.

According to this configuration, when force is applied directly or indirectly from the connecting portion 13 of the device 1 to the optical portion 20, since the U-shaped reinforcing member 41 is open or closed whereby the circumferential portion 22 of the optical portion 20 is deformed, the curvature of the optical portion 20 can be changed effectively.

Figure 10A:
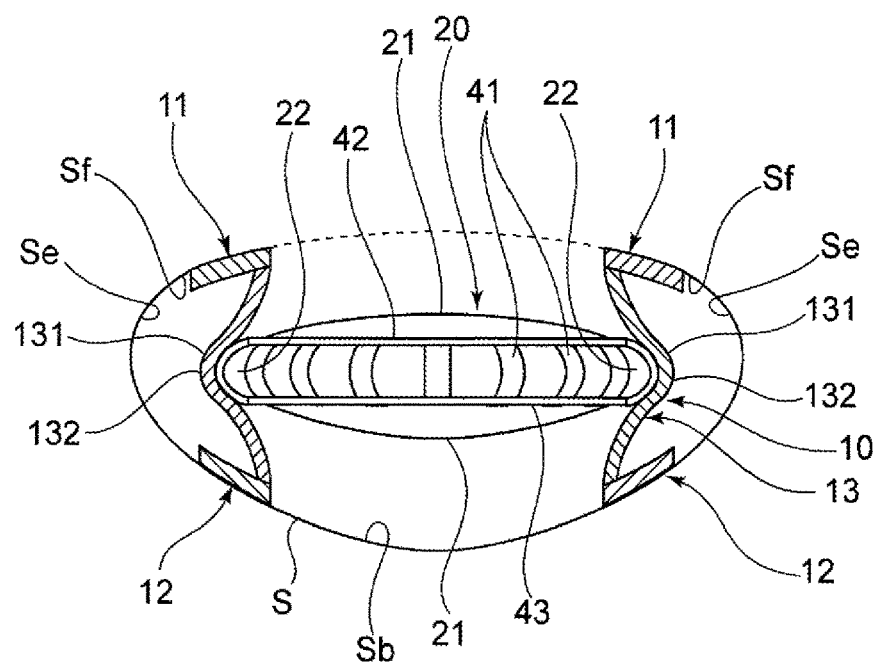
FIG. 10(a) is a longitudinal cross-sectional view of an accommodating intraocular lens according to a sixth embodiment.
Figure 10B:
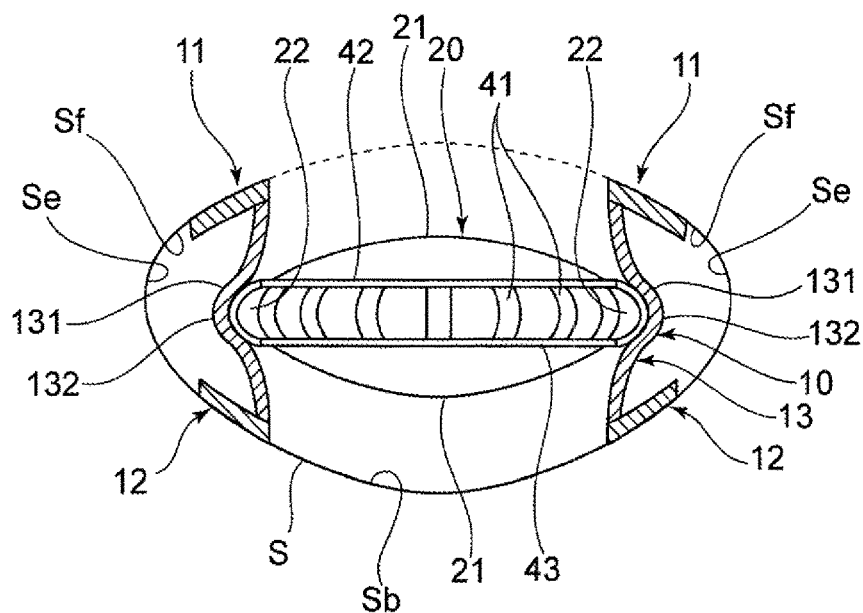
FIG. 10(b) is a longitudinal cross-sectional view of an accommodating intraocular lens according to a sixth embodiment.

Moreover, as illustrated in FIG. 10, the reinforcing member 40 further includes a front reinforcing ring member 42 provided on a front outer surface of the optical portion 20 and a rear reinforcing ring member 43 provided on a rear outer surface of the optical portion. The front reinforcing ring member 42 and the rear reinforcing ring member 43 are connected by the U or V-shaped reinforcing member 41. According to this configuration, since the circumferential portion 22 of the optical portion 20 is deformed more reliably when the U or V-shaped reinforcing member 41 is stably open or closed, the curvature of the optical portion 20 can be changed more effectively.

In the present embodiment, although the reinforcing member is provided on the outer surface of an elastic film 23 of the optical portion 20, the reinforcing member may be provided on the inner surface of the elastic film 23.

Moreover, although the reinforcing member includes the front reinforcing ring member 42 and the rear reinforcing ring member 43, only one of the reinforcing ring members may be provided, and no reinforcing ring member may be provided.

Seventh Embodiment

Next, a tenth embodiment of the accommodating intraocular lens 1 according to the present invention will be described with reference to FIG. 11.

Figure 11A:
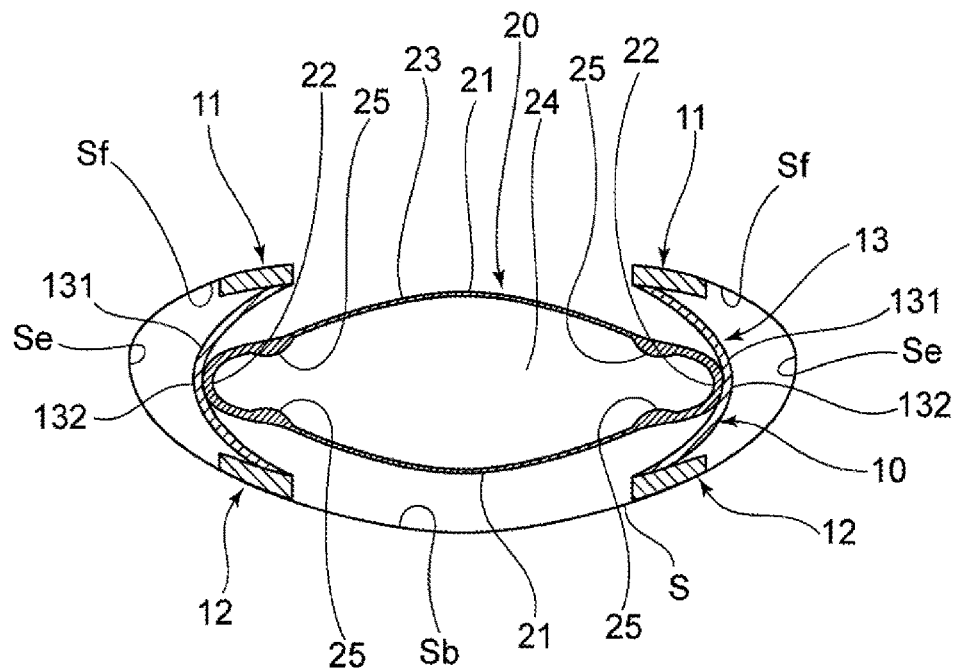
FIG. 11(a) is a longitudinal cross-sectional view of an accommodating intraocular lens according to a seventh embodiment.

As illustrated in FIG. 11(a), the optical portion 20 according to the present embodiment is formed of an elastic film 23 which can be expanded and contracted and has a predetermined thickness, and a flowable substance 24 is filled in the elastic film 24. In particular, in the present embodiment, the circumferential portion 22 of the optical portion 20 has a thickness of 20 to 100 µm, the central portions on the front and rear sides have a thickness of 5 to 20 µm, and the circumferential portion 22 is thicker than the central portions 21 on the front and rear sides. According to this configuration, a local deformation of the circumferential portion 22 of the optical portion 20 decreases, and the circumferential portion 22 is likely to be deformed generally uniformly. As a result, the central portions 21 on the front and rear sides of the optical portion 20 are also likely to be deformed uniformly. Moreover, since the central portions 21 on the front and rear sides of the optical portion 20 are likely to be deformed due to a small thickness, the curvature of the optical portion 20 can be changed effectively.

Figure 11B:
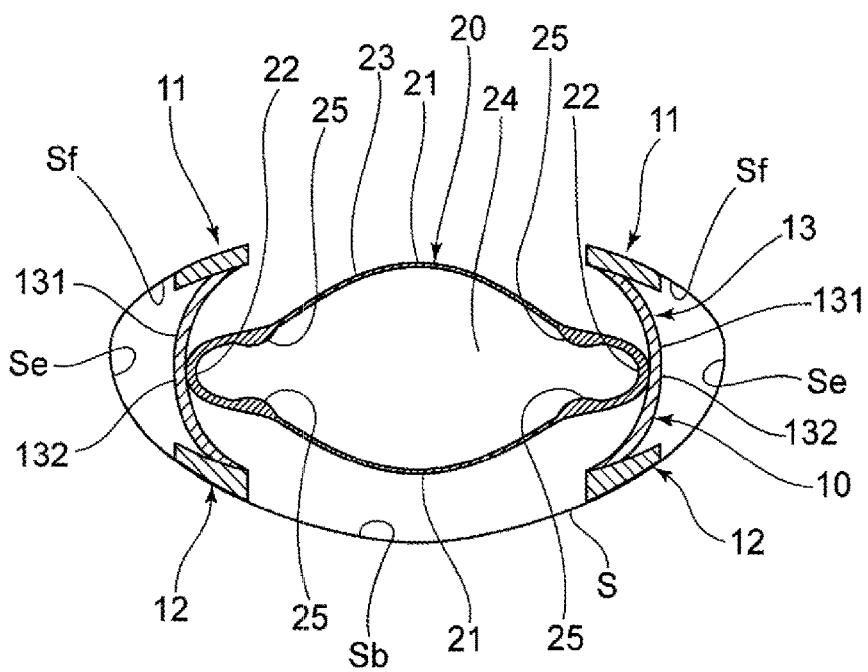
FIG. 11(b) is a longitudinal cross-sectional view of an accommodating intraocular lens according to a seventh embodiment.

Moreover, as illustrated in FIG. 11(a), the optical portion 20 may have a bulging portion 25 on the inner surface of the upper and lower sides of the circumferential portion 22. Due to this, as illustrated in FIG. 11(b), when the circumferential portion 22 is pressed in an inward direction by the connecting pieces 131, the elastic film 23 is easily constricted near the bulging portion 25, and the curvature of the central portion 21 can be changed efficiently.

In the present embodiment, although the circumferential portion 22 is formed thicker than the central portions 21 on the front and rear sides, the elastic film may be formed so that the thickness thereof gradually decreases as it advances from the circumferential portion toward the central portion.

Modification of Seventh Embodiment

Figure 12:
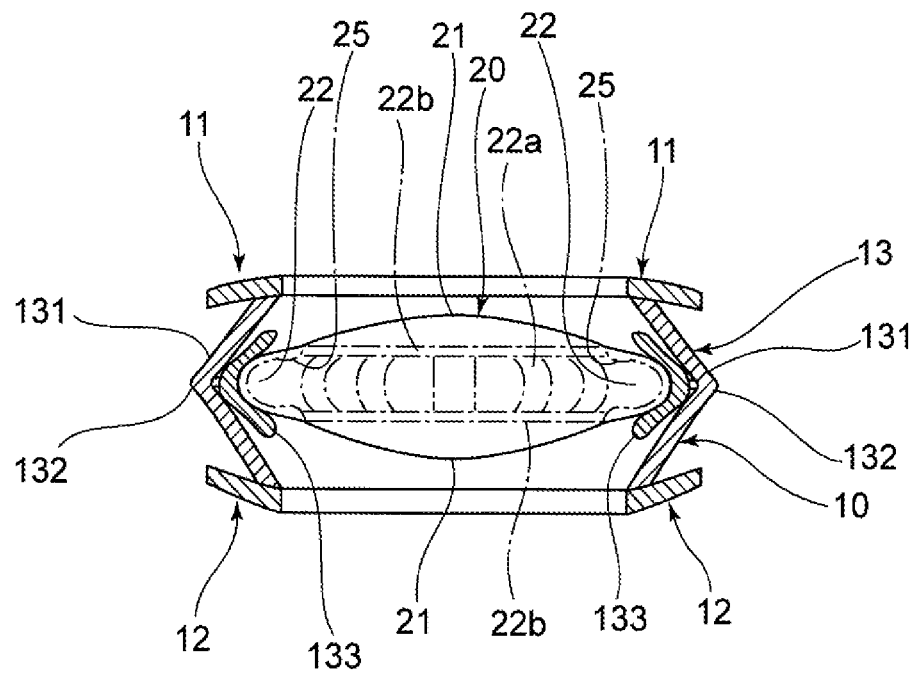
FIG. 12 is a longitudinal cross-sectional view of an accommodating intraocular lens according to a modification of the seventh embodiment.

As illustrated in FIG. 12, in the optical portion 20 according to this modification, a plurality of thick portions 22a where the elastic film 23 has a large thickness is provided at predetermined intervals along the circumferential portion 22 of the optical portion 20. According to this configuration, a local deformation of the circumferential portion 22 of the optical portion 20 decreases, and the circumferential portion 22 is likely to be deformed generally uniformly. As a result, since the central portions 21 on the front and rear sides of the optical portion 20 are also likely to be deformed uniformly, the optical quality of the optical portion 20 is improved and the curvature of the optical portion 20 can be changed effectively.

As illustrated in FIG. 12, in the optical portion 20, the thick portions 22a may be connected to each other by ring-shaped thick portions 22b provided before and after the thick portion 22a.

Eighth Embodiment

Figure 13:
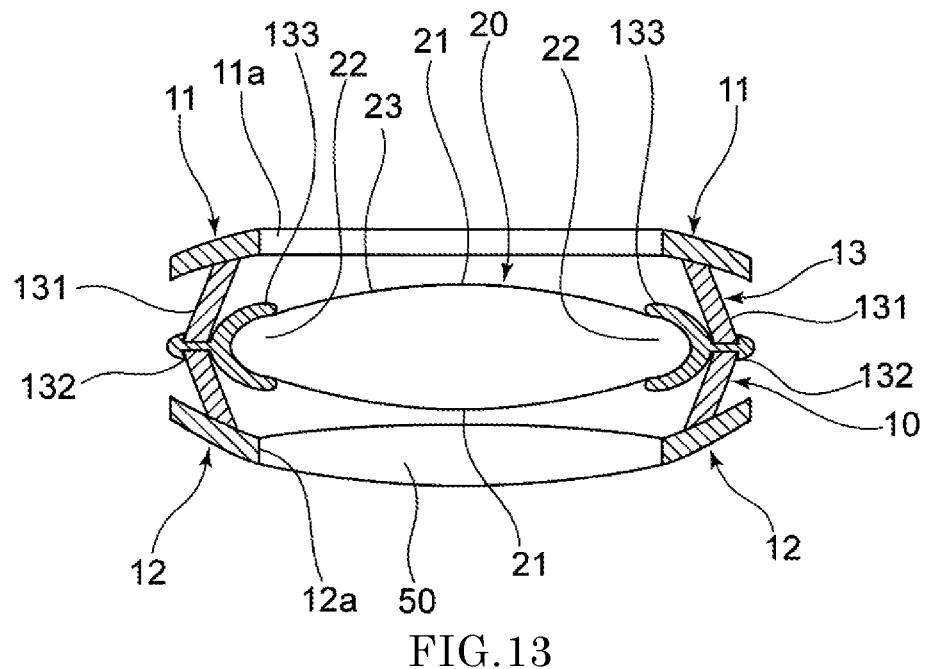
FIG. 13 is a longitudinal cross-sectional view of an accommodating intraocular lens according to an eighth embodiment.

Next, an eighth embodiment of the accommodating intraocular lens 1 according to the present invention will be described with reference to FIG. 13.

In the accommodating intraocular lens 1 according to the present embodiment, a convex lens 50 is fitted into the opening 12a of the rear supporting portion 12. According to this configuration, the optical portion 20 can be used for the purpose of obtaining the accommodation power mainly and the convex lens 50 provided in the rear supporting portion 12 can be used for the purpose of obtaining a refractive power corresponding to the symptom of a patient. Due to this, the optical portion 20 is easily folded when it is formed in a flat shape and can be inserted into the eye from a small incised wound of the lens capsule S. Moreover, since the convex lens 50 provided in the rear supporting portion 12 supplements the refractive power after surgery mainly, it is possible to reduce a refraction error (a difference between a target refractive value before surgery and an actual refractive value after surgery) of the refractive power after surgery.

In the present embodiment, although the convex lens 50 is fitted into the opening 12a of the rear supporting portion 12, the convex lens 50 may be fitted into the opening 11a of the front supporting portion 11.

Moreover, although the convex lens 50 is fitted into the opening 12a of the rear supporting portion 12, a concave lens may be fitted into the opening 12a.

Ninth Embodiment

Next, a ninth embodiment of the accommodating intraocular lens 1 according to the present invention will be described with reference to FIG. 14.

Figure 14:
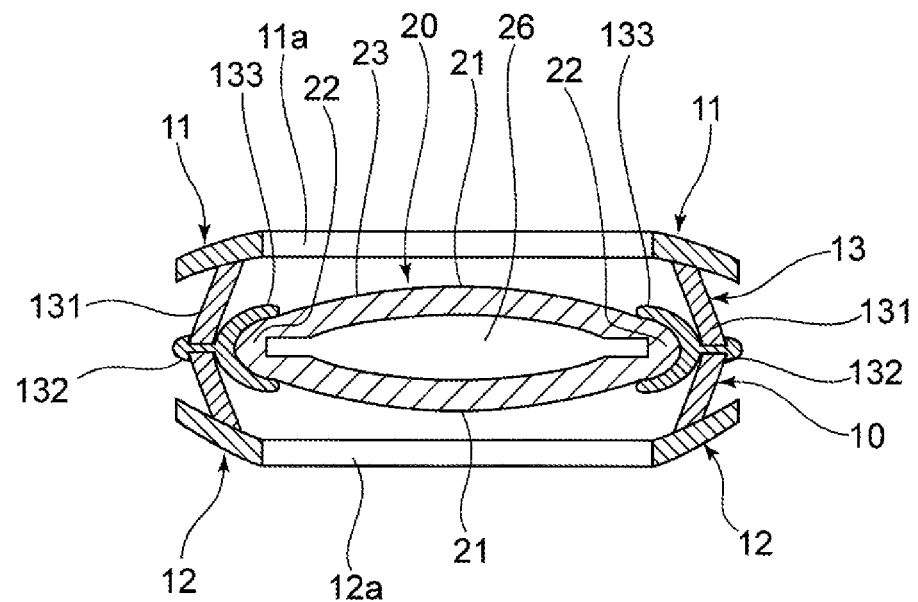
FIG. 14 is a longitudinal cross-sectional view of an accommodating intraocular lens according to a ninth embodiment.

As illustrated in FIG. 14, the optical portion 20 according to the present embodiment further includes a convex lens 26. According to this configuration, the optical portion 20 can be used for the purpose of obtaining the accommodation power mainly and the convex lens 26 provided in the optical portion 20 can be used for the purpose of obtaining a refractive power corresponding to the symptom of a patient. Moreover, it is possible to reduce a refraction error (a difference between a target refractive value before surgery and an actual refractive value after surgery) of the refractive power after surgery. Moreover, since the convex lens provided in the optical portion corresponds to the embryonic nucleus of a human lens, it is possible to change the curvature of the optical portion more effectively.

Tenth Embodiment

Next, a tenth embodiment of the accommodating intraocular lens 1 according to the present invention will be described with reference to FIG. 15.

Figure 15:
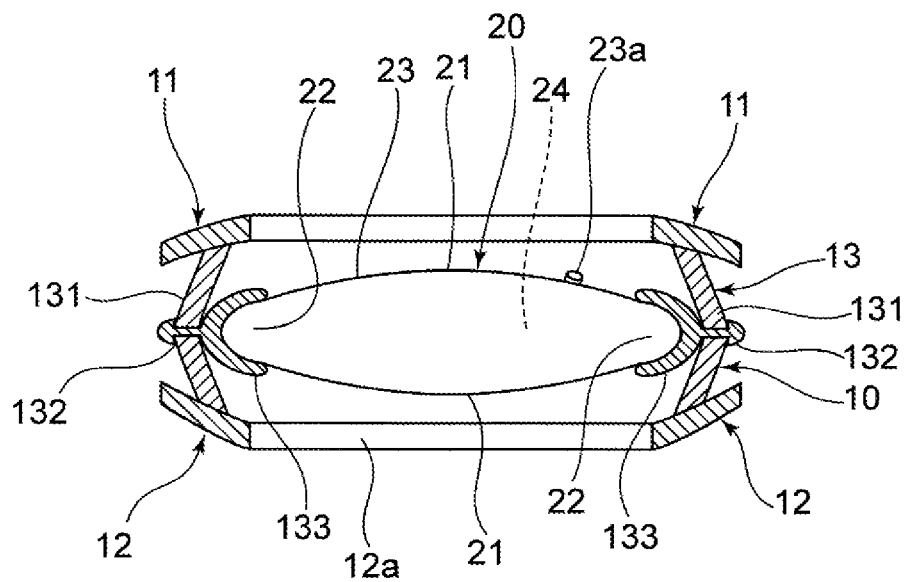
FIG. 15 is a longitudinal cross-sectional view of an accommodating intraocular lens according to a tenth embodiment.

As illustrated in FIG. 15, in the optical portion 20 according to the present embodiment, an injector 23a for injecting a flowable substance 24 therein is formed in the elastic film 23. According to this configuration, after the optical portion 20 is folded and inserted into the lens capsule expanding device 10 in a state in which no or a small amount of the flowable substance 24 is present in the optical portion 20, since the flowable substance 24 can be injected into the optical portion 20 through the injector 23a, it is possible to reduce the size of an incised wound for inserting the accommodating intraocular lens 1 into the lens capsule S. Moreover, the refractive power after surgery can be easily adjusted to a target refractive power by injecting or sucking the flowable substance 24 from the injector when a refraction error occurs after surgery. A valve for preventing backflow of the flowable substance 24 may be formed in the injector 23a.

Eleventh Embodiment

Next, an eleventh embodiment of the accommodating intraocular lens 1 according to the present invention will be described with reference to FIG. 16.

Figure 16:
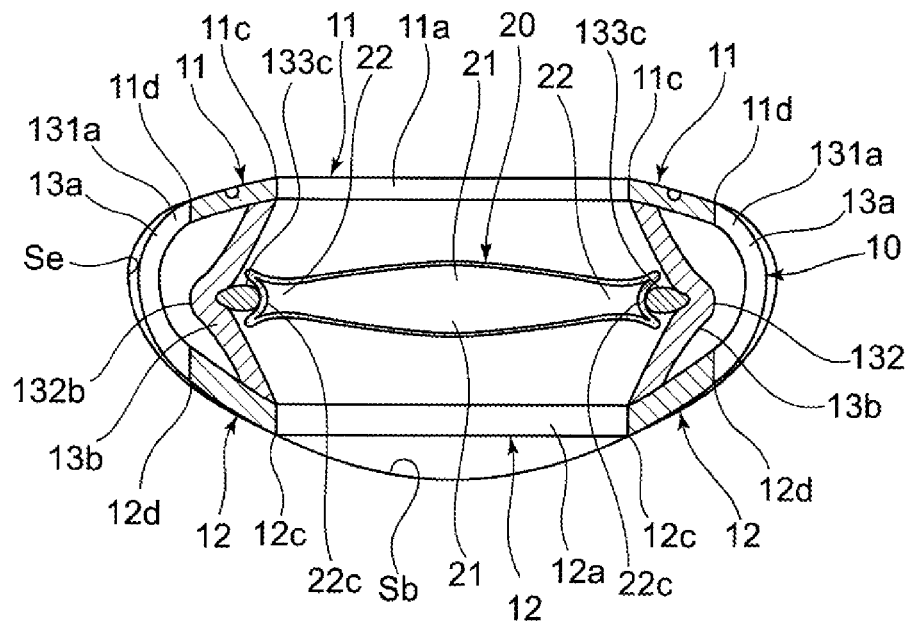
FIG. 16 is a longitudinal cross-sectional view of an accommodating intraocular lens according to an eleventh embodiment.

As illustrated in FIG. 16, the optical portion 20 according to the present embodiment is formed in such a manner that a side surface 22c of the circumferential portion 22 is depressed in a U-shape in the radially inward direction.

Moreover, as illustrated in FIG. 16, a rod-shaped locking member 133c is formed in the device 10 according to the present embodiment and the locking member 133c locks the circumferential portion of the optical portion 10 in such a manner as to press the circumferential portion from the radial direction.

According to this configuration, even when the optical portion 20 is formed of a relatively rigid member which is elastically deformable, it is possible to reliably lock the circumferential portion 22 of the optical portion 20 and to arrange the optical portion 20 stably in the device 1.

Twelfth Embodiment

Next, a twelfth embodiment of the accommodating intraocular lens 1 according to the present invention will be described with reference to FIG. 17.

Figure 17:
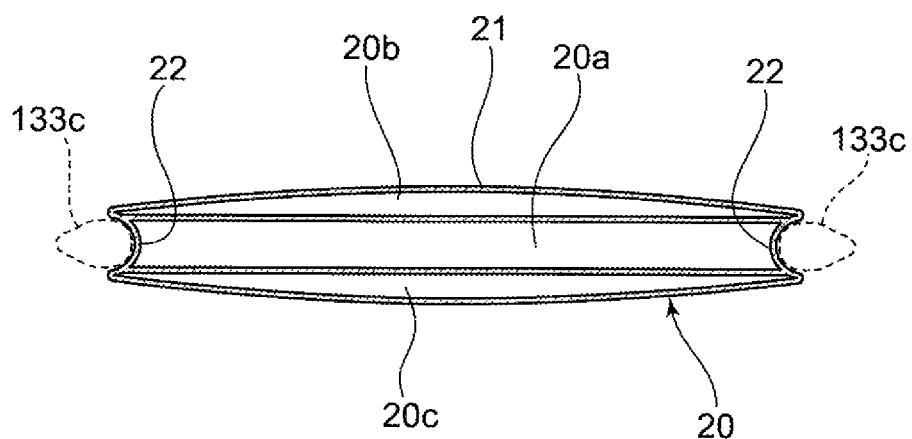
FIG. 17 is a longitudinal cross-sectional view of an optical portion of an accommodating intraocular lens according to a twelfth embodiment.
Figure 18A:
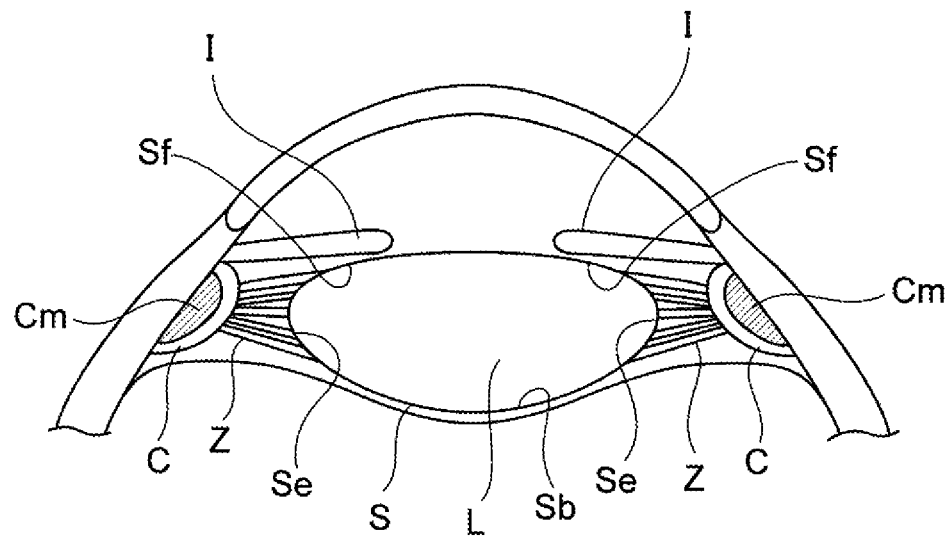
FIG. 18(a) is a side view illustrating the movement of human eyes during focus accommodation.
Figure 18B:
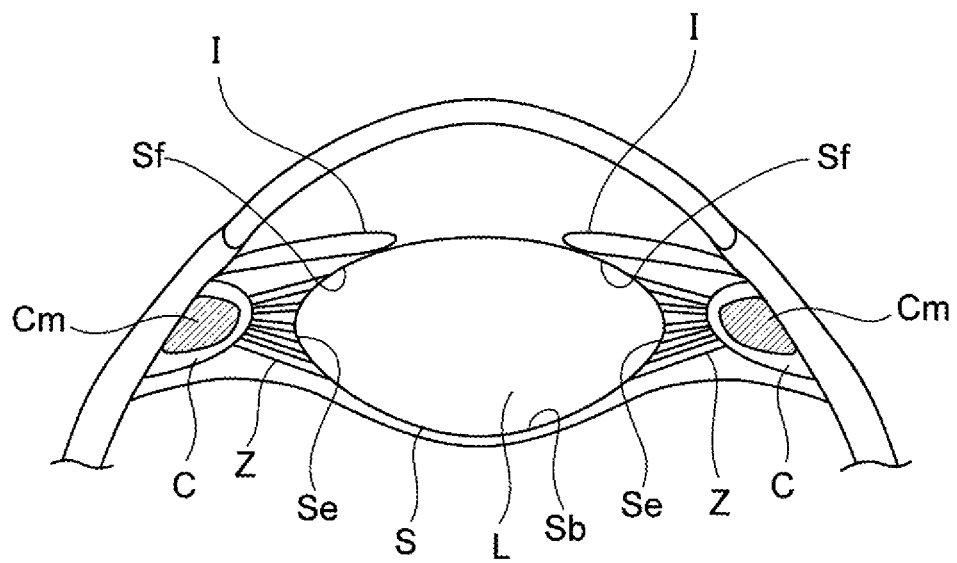
FIG. 18(b) is a side view illustrating the movement of human eyes during focus accommodation.

As illustrated in FIG. 17, the optical portion 10 according to the present embodiment is partitioned into three layers in the front-back direction, and a segment 20a including the center of the optical portion 20 has a larger refractive index than the refractive indices of the segments 20b and 20c on the other layers. For example, a flowable substance which is silicon oil having a refractive index of 1.44 is filled into the segment 20a including the center of the optical portion 20, and a flowable substance which is silicon oil having a refractive index of 1.41 is filled into the segments 20b and 20c on the front and rear sides. According to this configuration, since the closer to the center, the larger the refractive index like a human lens, it is possible to create a large change in the refractive index by a small deformation of the optical portion 20.

In the present embodiment, although the refractive index of the focus accommodation is changed by partitioning the optical portion 10, the optical portion 10 may be formed so that the refractive index of the flowable substance gradually increases toward the center of the optical portion 10 according to other methods.

While the embodiments of the present invention have been described with reference to the drawings, the present invention is not limited to the illustrated embodiments. Various changes or modifications can be made to the illustrated embodiments within the same scope as the present invention or its equivalent range.

The invention claimed is:

1. An accommodating intraocular lens (IOL) configured to be inserted into a lens capsule from which contents are removed during an ophthalmic surgery, comprising:
   a lens capsule expanding device; and
   an optical portion arranged centrally within the lens capsule expanding device, the optical portion comprising an anterior convex surface, a posterior convex surface, a central portion, and a circumferential portion, the optical portion being elastically deformable, the lens capsule expanding device comprising:
   a front ring-shaped supporting portion comprising an anterior capsular-engaging circumferential surface provided in such a manner as to make contact with an inner surface of an anterior capsule so as to pass light toward a rear side of the intraocular lens, the anterior capsular-engaging circumferential surface gradually inclined toward the rear side of the intraocular lens as it advances from an inner circumferential portion of the front ring-shaped supporting portion toward an outer circumferential portion of the front ring-shaped supporting portion, the front ring-shaped supporting portion further comprising radial notches extending from the inner circumferential portion toward the outer circumferential portion;
   a rear ring-shaped supporting portion comprising a posterior capsular-engaging circumferential surface provided in such a manner as to make contact with an inner surface of a posterior capsule while facing the front supporting portion so as to pass light from a front side of the intraocular lens toward the rear side of the intraocular lens, the posterior capsular-engaging circumferential surface gradually inclined toward the front side of the intraocular lens as it advances from an inner circumferential portion of the rear ring-shaped supporting portion toward an outer circumferential portion of the rear ring-shaped supporting portion; and
   a connecting portion placed between the front ring-shaped supporting portion and the rear ring-shaped supporting portion, the connecting portion comprising:
   a plurality of discrete connecting thin plate members formed of an elastic material and provided at equal intervals in the circumferential direction of the front ring-shaped supporting portion and the rear ring-shaped supporting portion, the plurality of discrete connecting thin plate members connecting the inner circumferential portion of the front ring-shaped supporting portion and the inner circumferential portion of the rear ring-shaped supporting portion in such a manner as to have biasing force in a direction of separating the front ring-shaped supporting portion and the rear supporting portion from each other,
   a bent portion formed in the connecting portion at each of the plurality of discrete connecting thin plate members so as to be bent in such a manner as to expand in a radially outward direction of the front ring-shaped supporting portion and the rear ring-shaped supporting portion, and
   a plurality of U-shaped or V-shaped locking members provided on an inner side of the bent portion of the connecting portion at each of the plurality of discrete connecting thin plate members,
   wherein
   due to the biasing force of the connecting portion, the front ring-shaped supporting portion is configured to press the inner surface of the anterior capsule and the rear ring-shaped supporting portion is configured to press the inner surface of the posterior capsule, and
   the circumferential portion of the optical portion is locked directly to the plurality of U-shaped or V-shaped locking members of the bent portion of the connecting portion in such a manner that the optical portion is surrounded by the connecting portion of the lens capsule expanding device, and force is applied directly or indirectly in a radial direction from the connecting portion to the circumferential portion of the optical portion according to movement of the connecting portion when the front ring-shaped supporting portion and the rear ring-shaped supporting portion move in a direction closer to or away from each other with movement of the lens capsule whereby a curvature of the optical portion is changed,
   wherein the plurality of U-shaped or V-shaped locking members are open in a radially inward direction of the optical portion so as to lock the circumferential portion of the optical portion by sandwiching the circumferential portion from a front-back direction,
   wherein the optical portion is formed of an elastic film that can be expanded and contracted, and has a predetermined thickness, and a flowable optical substance is filled in the elastic film,
   wherein the elastic film of the circumferential portion of the optical portion is thicker than the elastic film of the central portion of the optical portion,
   wherein the optical portion is formed so that the thickness of the elastic film gradually increases as it advances from the central portion toward the circumferential portion, and
   wherein the optical portion is formed so that a refractive index of the flowable optical substance gradually increases toward a center of the optical portion.

2. The accommodating intraocular lens according to claim 1, wherein
   the elastic film of the circumferential portion of the optical portion has a thickness of 20 μm to 100 μm, the elastic film of the central portion of the optical portion has a thickness of 5 μm to 20 μm.

3. The accommodating intraocular lens according to claim 1, wherein
the optical portion has an injector for injecting the flowable substance into the optical portion.

* * * * *